US008574630B2

(12) United States Patent
Wu et al.

(10) Patent No.: US 8,574,630 B2
(45) Date of Patent: Nov. 5, 2013

(54) CORTICOSTEROID PARTICLES AND METHOD OF PRODUCTION

(75) Inventors: Libo Wu, Mountain View, CA (US); Wiwik Watanabe, Union City, CA (US); Jian Zhang, Sunnyvale, CA (US)

(73) Assignee: MAP Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 13/237,792

(22) Filed: Sep. 20, 2011

(65) Prior Publication Data

US 2012/0135046 A1 May 31, 2012

Related U.S. Application Data

(60) Provisional application No. 61/403,941, filed on Sep. 22, 2010.

(51) Int. Cl.
*A61K 9/14* (2006.01)
*A61K 31/58* (2006.01)
*C07J 71/00* (2006.01)

(52) U.S. Cl.
USPC .............. 424/489; 424/400; 514/174; 540/63

(58) Field of Classification Search
None
See application file for complete search history.

(56) References Cited

U.S. PATENT DOCUMENTS

| | | | | |
|---|---|---|---|---|
| 5,510,118 | A | 4/1996 | Bosch et al. | |
| 5,518,187 | A | 5/1996 | Bruno et al. | |
| 5,709,884 | A | 1/1998 | Trofast et al. | |
| 5,718,388 | A | 2/1998 | Czekai et al. | |
| 5,758,637 | A | 6/1998 | Ivri et al. | |
| 5,862,999 | A | 1/1999 | Czekai et al. | |
| 5,874,063 | A | 2/1999 | Briggner et al. | |
| 5,938,117 | A | 8/1999 | Ivri | |
| 6,085,740 | A | 7/2000 | Ivri et al. | |
| 6,221,398 | B1 | 4/2001 | Jakupovic et al. | |
| 6,235,177 | B1 | 5/2001 | Borland et al. | |
| 6,346,523 | B1 * | 2/2002 | Bisrat et al. | 514/172 |
| 6,467,476 | B1 | 10/2002 | Ivri et al. | |
| 6,554,201 | B2 | 4/2003 | Klimowicz et al. | |
| 6,915,962 | B2 | 7/2005 | Power et al. | |
| 7,032,590 | B2 | 4/2006 | Loeffler et al. | |
| 7,066,398 | B2 | 6/2006 | Borland et al. | |
| 2002/0102294 | A1 | 8/2002 | Bosch et al. | |
| 2003/0049323 | A1 | 3/2003 | Hitt et al. | |
| 2004/0197275 | A1 | 10/2004 | Jongen et al. | |
| 2006/0188579 | A1 | 8/2006 | Rogueda | |
| 2007/0197487 | A1 | 8/2007 | Hill | |
| 2008/0058374 | A1 | 3/2008 | Mu et al. | |
| 2009/0149432 | A1 | 6/2009 | Shrewsbury et al. | |
| 2009/0157037 | A1 | 6/2009 | Iyer et al. | |

FOREIGN PATENT DOCUMENTS

WO WO2008005053 A1 1/2008

OTHER PUBLICATIONS

Troy, D.B., Editor. Remington: The Science and Practice of Pharmacy, 21st Edition. Baltimore: Lippincott, Williams and Wilkens, 2006, p. 738.*

U.S. Pharmacopeia, vol. 29-NF24, downloaded from the site: http://www.pharmacopeia.cn/v29240/usp29nf24s0_c941.html on May 19, 2013.*

Leflein, et al., Delivery of glucocorticoids by jet nebulization: Aerosol characteristics and output. J Allergy and Clinical Immunology, 1995, 95(5):944-949, abstract, p. 948 section titled Discussion; p. 945, 947; Fig 1.

Bosco, et al., A Novel Budesonide Formulation for Nebulization Significantly Improves the Amount of Drug Emitted over One Minute in a Simulated Pediatric Tidal Breathing Model. Abstract pB31. Asthma Therapeutics-Studies in Humans. Am J Respir Crit Care Med 2009, 179:A2790. [retrieved from the Internet Mar. 12, 2012: <http://ajrccm.atsjournals.org/cgi/reprint/179/1_MeetingAbstracts/A2790>]; in entirety.

Hockhaus, G., (2007) Annals of Allergy, Asthma and Immunology, 98:S7-S15.

Suarez, et al., (1998) Pharm Res., 15:461-465.

Barnes (2003) Ann Intern Med,139:359-370.

Velaga, et al., (2002) Pharmaceutical Research, 19(10):1564-1571.

Steckle, et al. (2004) European Journal of Pharmaceutics and Biopharmaceutics, 57:507-512.

Hu, et al. (2008) Ind. Eng. Chem. Res., 47:9623-9627.

Ruch, et al. (2000) Journal of Colloid and Interface Science, 229:207-211.

Brunauer, et al. (1938) J. Am. Chem. Soc., 60:309.

Freiwald, et al. (2005) Respiratory Research, 6:21.

R. Dhand, Respiratory Care (Dec. 2002) 47(12), p. 1406-1418.

Heyder, et al. (1986) Aerosol Sci.,17:811-825.

Cipolla, et al. (1994) S.T.. Pharma Sciences, 4(1):50-62.

(Continued)

*Primary Examiner* — Frederick Krass
*Assistant Examiner* — Michael P Cohen
(74) *Attorney, Agent, or Firm* — Jennifer C. Cheng

(57) ABSTRACT

A new particle morphology of glucocorticosteroids is described. The forms have a particle morphology that is particularly well suited for use in an inhaled corticosteroid drug suspension formulation for delivery from a next generation nebulizer device. Use of the new glucocorticosteroid particles enables enhanced drug delivery efficiency and increased residence time of the delivered drug in the lungs. New methods for producing glucocorticosteroid particles having these specific particle morphologies are also described. The methods provide a simplified, reproducible and scalable particle formation process that can produce glucocorticosteroid particles having a narrow particle size and shape distribution, a low surface energy, a low aspect ratio, uniform particle morphology and a reduced specific surface area.

26 Claims, 11 Drawing Sheets

(56) References Cited

OTHER PUBLICATIONS

Talton, et al. (2000) "Nano-thin coatings for improved lung targeting of glucocorticoid dry powders", Respiratory Drug Delivery VII, May 14-18, 2000, Florida.
Brogden, et al. (1992) Drugs 44:375-407.
Campbell, LM (1997) Drugs 58 (Suppl 4):25-33.
PCT International Search Report & Written Opinion, mailed Feb. 1, 2012, for PCT/US2011/052398 filed Sep. 20, 2011, 8 pgs.
PCT International Search Report & Written Opinion, mailed Mar. 23, 2012, for PCT/US2011/052397 filed Sep. 20, 2011, 10 pgs.
Requirement for Restriction/Election mailed Feb. 19, 2013, for U.S. Appl. No. 13/237,725, filed Sep. 20, 2011, 6 pages.
Response to Requirement for Restriction/Election filed Apr. 15, 2013, for U.S. Appl. No. 13/237,725, filed Sep. 20, 2011, 8 pages.

* cited by examiner

Square bifrustum-shaped budesonide particles

CORTICOSTEROID PARTICLES AND METHOD OF PRODUCTION

CROSS REFERENCE TO RELATED CASES

This application claims the benefit of the U.S. Provisional Patent Application Ser. No. 61/403,941, filed on Sep. 22, 2010, the content of which is hereby incorporated by reference in its entirety.

TECHNICAL FIELD OF THE INVENTION

The invention relates generally to technologies for producing and administering particulate medicaments via oral pulmonary inhalation and, more particularly, to methods for producing glucocorticosteroid particles with enhanced physical properties that facilitate delivery via pulmonary inhalation techniques using nebulizer inhalation devices, as well as the glucocorticosteroid particles themselves.

BACKGROUND OF THE INVENTION

Respiratory disorders are pulmonary conditions characterized by airway inflammation, airway hyperresponsiveness, and reversible airway obstruction. During respiratory disorder episodes, afflicted individuals often experience labored breathing, wheezing, and coughing. These disorders may be treated by oral inhalation of medications such as beta adrenergic agonists or corticosteroids.

Inhaled corticosteroids (ICS) are corticosteroid medicaments that are designed for application directly to the tissues of the respiratory tract. ICS medicaments are the preferred treatment for long-term control of mild persistent, moderate persistent, or severe persistent asthma symptoms in children, teens, and adults. Corticosteroids provide highly effective treatment for chronic inflammatory disorders through a common mechanism that includes down-regulating the production of many inflammatory cytokines, chemokines, enzymes, and cell-adhesion molecules as well as inhibiting the activity of inflammatory mediators. Barnes (2003) *Ann Intern Med* 139:359-370. Corticosteroids also help control narrowing and inflammation in the bronchial tubes. The drugs used as ICS are very similar in action and use. Commercially available ICS medicaments include Aerobid (flunisolide, Roche), Azmacort (triamcinolone acetonide, Abbott), Flovent (fluticasone propionate, GlaxoSmithKline), Pulmicort (budesonide, AstraZeneca) and QVAR (beclomethasone dipropionate, TEVA Branded Pharmaceuticals).

Delivery systems that can administer ICS medicaments include nebulizers, dry powder inhalers (DPIs), and pressurized metered-dose inhalers (pMDIs). Nebulizer devices are a preferred delivery system when breathing strength or coordination is challenging. This is particularly true for children, elderly patients and patients with compromised breathing ability.

Drug formulations for oral inhalation delivery using nebulizers are aqueous solutions, dispersions or suspensions that are aerosolized and then inhaled. The aerosol comprises very fine droplets of the formulation dispersed in air. The droplets are necessarily less than about 5 microns in geometric diameter to provide respirable droplets that enable delivery of the aerosolized drug to the respiratory tract beyond the oropharynx upon inhalation. Aerosol generators, or nebulizers, apply mechanical shearing forces to the drug formulation by various means to break up the formulation surface or generate filament streams to form the droplets. Nebulizers typically use pneumatic, piezoelectric, ultrasonic, or electromechanical means to generate shearing forces. The nebulizers may also incorporate baffling mechanisms to remove larger, non-respirable droplets from the aerosol. In use, the nebulized formulation is administered to the individual via a mouthpiece or mask.

Traditional nebulizer devices, such as jet nebulizers, are commonly used for ICS delivery. However, these devices require extended administration time lasting up to 30 minutes, often resulting in low patient compliance. In addition, the uniformity of the delivered dose from jet nebulizers can be challenging especially for suspension-based formulations. A particular group of nebulizers, referred to herein as "next generation nebulizers", use meshes or membranes to produce fine droplet sprays. These devices are much more efficient at producing aerosols, and can significantly reduce administration time. The meshes/membranes in next generation nebulizers contain many apertures or pores that have diameters typically between 1 and 8 microns. The drug formulation is forced through the mesh apertures by piezoelectric or electromechanical "pumping" or, alternatively, the mesh is vibrated to reciprocate through a pool of the formulation, thereby generating multiple liquid filaments with diameters approximating the mesh apertures. The filaments breakup to form droplets with diameters approximating the diameters of mesh apertures. Next generation nebulizers which include, but are not limited to the AerX and Essence devices (Aradigm Coorp., Hayward, Calif.), the eFlow device (PARI Respiratory Equipment, Monterey, Calif.), the TouchSpray device (The Technology Partnership, Cambridge, UK), the Ineb and Myneb devices (Respironic, Andover, Mass.), the MicroAir device (Omron Healthcare, Inc., Vernon Hills, Ill.) and the Aeroneb device (Aerogen, San Francisco, Calif.) are very efficient aerosol generators that minimize the duration of administration. This is because next generation nebulizers can form aerosols that have a high proportion of respirable aerosol droplets, those with diameters much less than 4.7 microns mass median aerodynamic diameter (MMAD per compendial method USP 601), enabling quick and efficient delivery of the aerosolized drug to the respiratory tract.

Use of next generation nebulizers to deliver a suspension-based medicament presents significant pharmaceutical formulation challenges in regard to the need to enhance both delivery efficiency to the lungs and drug residence time in the lungs. The first challenge is the efficient delivery of the drug particles to the lung. This is primarily determined by the size of the largest dimension of the aerosol droplet population. The mean diameter of the aerosol droplet size distribution generated by the nebulizer must not exceed 4.7 microns MMAD to penetrate to the lungs. The drug particles need to be substantially smaller, less than 4 microns, than the droplets to be carried by the droplet aerosol into the lungs. Further the drug particles in the suspension must be able to pass through the small apertures of the nebulizer mesh/membrane in an efficient and reproducible manner. For example, while several commercial ICS products (e.g. Astra Zeneca's Pulmicort® or Teva's Budesonide Inhalation Suspension) have particles small enough to penetrate to the lung, they have low aerosolization efficiency when delivered using a next generation nebulizers such as the Aeroneb Go device (Aerogen). The drug particles in these suspension formulations are too large at circa 4 microns to easily pass through the mesh which has a mean aperture diameter of circa 3 microns. A majority of the particles are retained on the surface of the mesh and cannot pass through into the aerosol droplets. Such high drug particle retention is undesirable because the trapped particles block the flow of the formulation through the mesh and decrease the delivery rate, thus increasing both the drug delivery time and amount of drug loaded into the nebulizer necessary to achieve the required delivered dose. This results in higher treatment cost and long treatment times. In addition, the retained drug particles can mechanically interfere with operation of the next generation nebulizer by accumulating on the mesh, clogging the pores and eventually blocking drug output, which can disable the nebulizer. The retained drug may also affect consistency and uniformity of the delivered dose within a particular dosing session or when comparing across administration sessions.

The second challenge is achieving appropriate drug residence time in the lungs. Delivery of the drug to the lungs by itself is not sufficient to achieve treatment if the drug passes immediately through the lung to systemic circulations. Hockhaus, G. (2007)*Annals of Allergy, Asthma and Immunology* 98:S7-S15. Prolonging the residence time in the lung will increase pulmonary receptor selectivity to treat local inflammation and lower undesirable systemic receptor side effects such as endogenous hormone generation and resulting growth suppression. Suarez et al. (1998) *Pharm Res.* 15:461-465. This is primarily determined by the lipophilicity of the drug, and the effective surface area of the drug particle population, where individual particle size and morphology are the chief variables. Since most glucocorticosteroids have relatively similar lipophilicity, the drug particles used in ICS formulations need to have a morphology that combines a minimum specific surface area (SSA) with the largest possible particle size. Reduction in the SSA of each drug particle, and thus the effective surface area of the particle population, lowers the dissolution rate of the drug in epithelial lining fluid and lung tissue, thereby increasing residence time in the targeted biospace. The easiest way to reduce surface area of a particle population is to increase the size of the individual particles, but this is in direct conflict with reducing the drug particle size to enable nebulizing with a next generation mesh/membrane nebulizer. Increases in the particle size that result in a particle dimension approaching or exceeding the size of the apertures in the mesh/membrane will reduce delivery efficiency. Decreases in the particle size, such as molecular-complex solutions, submicron or nanometer particle size suspensions to accommodate passage through the mesh/membrane will markedly decrease particle residence time in the lungs.

The most commonly used techniques for producing particles for use in ICS formulations are traditional micronization processes. See, e.g., U.S. Pat. Nos. 5,510,118; 5,518,187; 5,718,388; and 5,862,999. Prolonged grinding as occurs in micronizing comminution results in a high energy powder and crystal lattice defects which lowers physicochemical stability by making the particle susceptible to crystallinity shifts and chemical degradation. In addition, micronization processes usually produce particles having irregular shapes and wide particle size distributions. Accordingly, even though the SSA of a particle produced using micronization techniques can be relatively low, the particle size distribution in the population is too broad, and there are an unacceptably high amount of large particles produced that will be retained on the nebulizer mesh when administered by next generation nebulizers, resulting in low delivery efficiency.

Precipitation processes can also be used to generate particles as described in U.S. Pat. No. 6,221,398. However, optimum crystal structure formation and optimum purity may not be obtained in precipitation processes. It is difficult to control particle size and distribution by precipitations processes without resorting to high shear regimes. Finally residual solvent in the particles can lead to changes in crystallinity, particle size and shape, and/or chemical stability.

Because micronization or precipitation also results in some amorphous regions in the resulting particles, a "conditioning" step as described in U.S. Pat. No. 5,709,884 or U.S. Pat. No. 5,874,063 is necessary in order to obtain a particle considered to be completely crystalline. In these processes, conditioning the comminuted or precipitated particles with water or organic vapors reduces stored energy in the particles, induces crystallization of amorphous regions and reduces specific surface area of the particles to 3-10 meter$^2$/gram.

Another technique that can be used to produce particles for ICS formulations is supercritical fluid technology. See, e.g., Velaga et al. (2002) *Pharmaceutical Research* 19(10):1564-1571; and Steckle et al. (2004) *European Journal of Pharmaceutics and Biopharmaceutics* 57:507-512. Use of supercritical fluid particle formation processes can produce regularly shaped, partly spherical particle morphologies, the process parameters need to be carefully monitored to obtain reproducible results. In addition, supercritical fluid techniques are typically quite complex, have limited batch sizes, and are expensive and usually challenging to scale-up. Solvent/anti-solvent precipitation techniques have also been used to produce ICS (budesonide) particles with various morphologies such as flakes, spindles, ellipsoids and octahedrons. See, e.g., Hu et al. (2008) *Ind. Eng. Chem. Res.* 47:9623-9627 and Ruch et al. (2000) *Journal of Colloid and Interface Science* 229:207-211. However, the particles produced by such precipitation methods have a relatively high aspect ratio and SSA and are thus expected to have a reduced residence time in the lungs.

Accordingly, there remains a need in the art for improved glucocorticosteroid particles for use in ICS formulations, where the formulations exhibit enhanced delivery efficiency when administered using a next generation nebulizer device, and the particles also have selected physicochemical properties (crystallinity, shape, specific surface area and energy, size and size distribution) that provide for optimum delivery to the lung and to increase residence time in the lungs after administration. There further remains a need in the art for a simplified, reproducible and scalable particle formation process that can produce glucocorticosteroid particles having a narrow particle size and shape distribution, low aspect ratio and a uniform particle morphology that reduces the particle SSA.

SUMMARY OF THE INVENTION

It is an object of the invention to provide stable, highly uniform crystalline, reduced surface area, low aspect ratio glucocorticosteroid drug particles. These drug particles have a morphology that is particularly well suited for use in an ICS drug suspension formulation for efficient delivery from a next generation nebulizer device, and have relatively slow dissolution rates to prolong residence time in the lung. New methods for producing glucocorticosteroid particles having these specific particle morphologies are also provided. More particularly, a new non-supercritical solvent/anti-solvent technique is described. The method provides a simplified, reproducible and scalable particle formation process that can produce glucocorticosteroid particles having a narrow particle size and shape distribution, a low surface energy, a low aspect ratio, uniform particle morphology and a reduced SSA.

In one aspect of the invention, a method for forming a particulate budesonide composition is provided. The method includes the step of dissolving the budesonide glucocorticosteroid in a solvent. The solvent is formed from a combination of a water-miscible solvent and a partially water-miscible solvent. A budesonide solution is thus formed, which is combined with an antisolvent that contains a dispersion enhancer. The budesonide solution and antisolvent are combined using agitation to produce particles of budesonide having a mean diameter of from about 1 to about 10 microns, a SSA of from about 1 to about 3 meters$^2$/gram, and a square bifrustum shape. In some variations, the method produces particles that have a mean diameter of from about 1 to about 10 microns and/or a SSA of from about 2 to less than 3 meters$^2$/gram. The partially water-miscible solvent can be ethyl acetate, isopropyl acetate, diethyl ether, dichloromethane, methyl ethyl ketone, methyl isobutyl ketone, and any mixture thereof, with ethyl acetate being preferred. The water-miscible solvent can be acetone, acetonitrile, methanol, ethanol, isopropanol, dimethyl sulfoxide, or mixtures thereof, with methanol being preferred. In certain variations, the antisolvent is water, for example, where the antisolvent comprises an aqueous solution of the dispersion enhancer. The dispersion enhancer can be polysorbate 20, polysorbate 40, polysorbate 60, polysorbate 80, polyethylene glycol, poloxamer, or mixtures thereof, with polysorbate 80 being preferred. The agitation step of the method can be carried out under conditions of high shear or high pressure, for example using a rotor-stator or high-pressure homogenizer apparatus. Mixing of the budesonide solution and the antisolvent is carried out at a temperature of from −10 to about 50° C., preferably where the antisolvent is cooled to 5° C. prior to combination with the budesonide solution. In certain variations, the antisolvent may include additional excipients such as a buffering agent, an isotonicity agent, and/or an antioxidant. If desired, the method of the invention can be carried out under sterile, or aseptic processing conditions, for example where the method includes the further steps of sterile filtration of the budesonide solution and the antisolvent.

In another aspect of the invention, new budesonide particles are provided having a novel crystal morphology. The particles are comprised of crystalline budesonide and have a mean diameter of from about 1 to about 10 microns, a SSA of from about 1 to about 3 meters$^2$/gram, and a square bifrustum shape. In some variations, the particles have a mean diameter of from about 1 to about 3 microns and/or a SSA of from about 2 to less than 3 meters$^2$/gram. In certain variations, the particles exhibit an in vitro dissolution rate of less than 90% cumulative release after 1 minute when measured in a USP dissolution apparatus Type II, where the dissolution medium is 500 mL of simulated epithelial lung fluid (SELF) at 37° C., with a stirring rate of 75 rpm under sink conditions.

In certain variations, the glucocorticosteroid particles of the invention can be converted into an ICS drug suspension formulation that is suitable for aerosol delivery, for example, by forming a suspension of the particles in an appropriate buffering solution such as sterile citrate-buffered isotonic saline solution. In other variations, the ICS aerosol formulations may include excipients and/or additives. Suitable excipients and/or additives that may be employed include buffering agents, isotonicity agents, dispersion enhancers, and antioxidants.

In certain variations, the aerosol ICS drug suspension formulation can be dosed into any suitable individual unit dose container including, for example, blisters, vials, ampoules, canisters, cartridges, and the like. The individual containers may be made from any suitable material that does not react with the formulation, and which does not allow substantial permeation of oxygen through the container wall. The containers can then be used in next generation nebulizers to administer the aerosol ICS drug suspension formulation.

It is a particular advantage of the present invention that improved glucocorticosteroid particles for use in aerosol ICS suspension formulations can be provided, where the formulations exhibit enhanced delivery efficiency when administered using a next generation nebulizer device. It is also a particular advantage of the present invention that simple and reproducible methods can be used to produce the particles of the invention.

These and other objects, aspects, variations and advantages of the present invention will readily occur to the ordinarily skilled practitioner upon reading the instant disclosure and specification.

BRIEF DESCRIPTION OF THE DRAWINGS

FIG. 5(*b*) shows images of square bifrustum-shaped budesonide particles produced according to the methods of the instant invention.

DETAILED DESCRIPTION OF THE INVENTION

Figure 1:
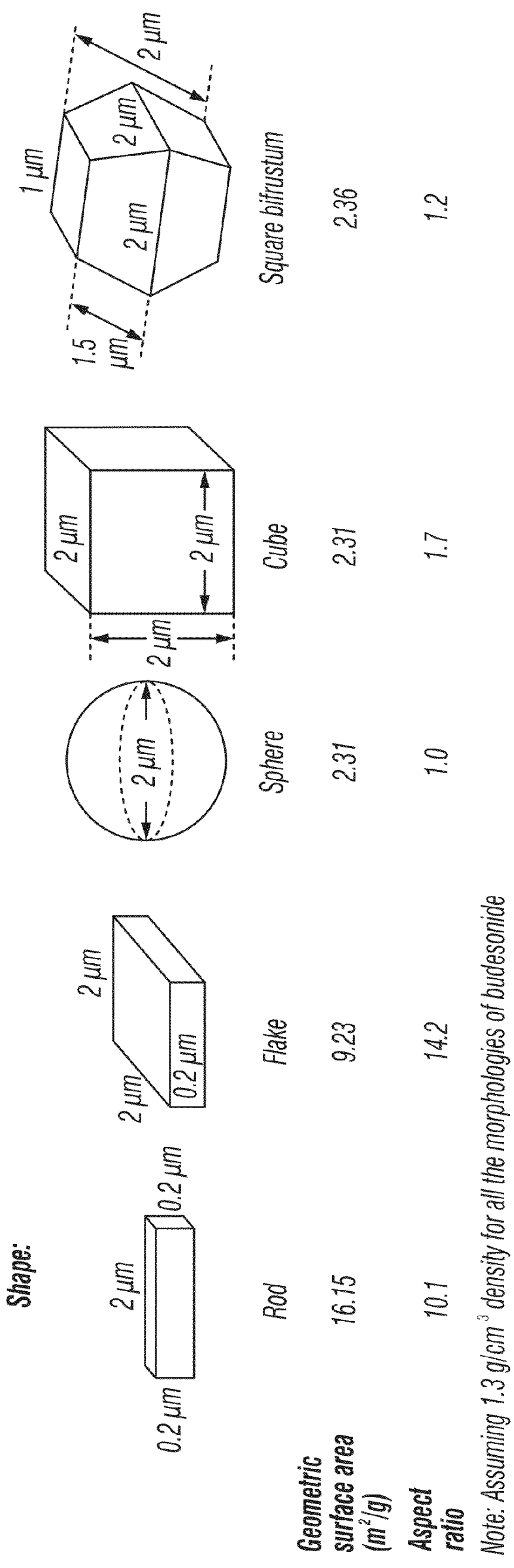
FIG. 1 depicts a series of theoretical budesonide particle morphologies (crystal shapes), each having a representative size of 2 microns, and the calculated specific surface areas (SSAs) and aspect ratio for each crystal shape assuming a density of 1.3 g/cm$^3$ for all budesonide morphologies.

Before describing the present invention in detail, it is to be understood that this invention is not limited to particularly exemplified glucocorticosteroid particles, ICS formulations, nebulizer devices, nebulizer components, or manufacturing process parameters as such may, of course, vary. It is also to be understood that the technical terminology used herein is for the purpose of describing particular embodiments of the invention only, and is not intended to be limiting.

All publications, patents and patent applications cited herein, whether supra or infra, are hereby incorporated by reference in their entirety.

Described herein are novel particle morphology and size distribution of glucocorticosteroids that is particularly well suited for use in an ICS drug suspension formulation for delivery from a next generation nebulizer device, providing for enhanced drug delivery efficiency and increased residence time of the delivered drug in the lungs. Also described herein are new methods for producing glucocorticosteroid particles having these specific particle morphologies. In particular, the two key aspects for ICS particles delivered by next generation nebulizers are delivery efficiency and residence time in lungs. Delivery efficiency through the next generation nebulizer mesh/membrane is determined by the size of the largest particle dimension. Residence time in lungs for ICS type drugs is controlled by the particle surface area which is determined by particle size and morphology (largest dimension, aspect ratio and SSA).

The glucocorticosteroid particles of the present invention have a unique morphology with minimum SSA and the largest feasible dimension size that still enables a majority of the particles to pass through the mesh/membrane in the next generation nebulizer, and preferably are highly uniform in both size and shape. These new glucocorticosteroid particle morphologies are particularly useful for incorporation into ICS formulations and in particular those formulations that are delivered using a next generation nebulizer, where they provide for shortened delivery time to maximize patient compliance, and minimized drug retention in the device and reduced dissolution rate (increased residence time in the lungs) to enhance therapeutic efficacy.

There are many factors which can affect the efficacy of ICS suspension formulations including efficient delivery to the lungs, receptor-binding affinity, formulation chemistry, mucociliary clearance and pulmonary residence time. Increasing pulmonary residence time of an ICS formulation in the lungs allows for extended duration of high drug concentrations in the lungs, and thus provides for enhanced drug efficacy. However, extending ICS residence time in the lungs can be very challenging due to: (1) the very large surface area of the lungs and thin membrane that allow for a quick exchange between the outer part of lungs and the blood circulation system; and (2) the lipophilicity of ICS drugs and any excipients in the formulation that can cause fast transport across the respiratory tract epithelium once dissolved in the epithelial lung fluid (ELF). One strategy that has been used to enhance pulmonary residence time for ICS formulations is to select a drug that has a higher lipophilicity, such as fluticasone propionate which slows particle dissolution in the ELF. However, this approach is drug-specific and therefore is not always achievable. Furthermore, while it slows dissolution in significantly enhances transport across the cell membrane increasing systemic exposure.

Another strategy that does not depend on changing the intrinsic properties of the drug, is to decrease the surface area of the drug particles to minimize the dissolution rate. This approach avoids potentially affecting intrinsic efficacy of the drug and minimizes the risk of high plasma concentration spikes in the systemic circulation due to rapid transport of dissolved drug across the epithelium. Rugosity is another factor that influences the surface area of a particle. Rugosity, expressed in the below formula as $f_r$, is a measure of small-scale variations or amplitude in height of a surface. Rugosity is also referred to as the measurement of the roughness of a surface (or surface profile). A mathematical representation of rugosity is:

$$f_r=A_r/A_g$$

where $A_r$ is the real or actual surface area and $A_g$ is the geometric surface area. In order to minimize dissolution rate, the rugosity of the drug particles should be as small as possible, meaning as smooth as possible. An increase in rugosity (rough surface area of the particle) will mean a larger surface area, and therefore a faster dissolution rate. A smooth particle surface (low rugosity) will minimize the dissolution rate of the particles and enhance pulmonary residence.

In order to increase the efficacy of ICS suspension formulations, it is a primary object of the present invention to provide corticosteroid particles having a morphology that provides the optimum size and shape for administration from a next generation nebulizer device. Accordingly, the particles of the present invention have a low aspect ratio (largest dimension to smallest dimension ratio), preferably an aspect ratio approaching 1; a low specific surface area (SSA, surface area to mass ratio), preferably in the range of from about 1 to about 5 $m^2$/gm, and more preferably in the range of about 2 to about 3 $m^2$/gm; and a mean particle diameter (largest particle dimension) preferably in the range of about 1 to about 10 microns, and more preferably in the range of about 1 to about 3 microns.

The SSA of particles produced according to the present invention can be measured by BET nitrogen absorption which is a commonly used technique to measure the surface area for pharmaceutical powders (Brunauer et al. (1938) *J. Am. Chem. Soc.* 60:309), or can be theoretically calculated using the surface area and known mass of the selected glucocorticosteroid material. Measurement of the various dimensions of particles produced according to the present invention can be determined using instruments and techniques that are well known in the art, for example by using an electrical zone sensing instrument such as a Multisizer IIe (Coulter Electronic, Luton, Beds, England), or a laser diffraction instrument, e.g., a Helos device (Sympatec, Princeton, N.J.). In this regard, the measured dimensions of particles in a particle population will be a range which depends, in part, upon the particle formation method utilized to produce the particles. Accordingly, the final overall distribution of size of particles in a population can be selected to fit the preferred ranges herein using standard particle size selection techniques such as sieving to remove large/small particle fractions from the final population.

The particular glucocorticosteroid selected for use in the particles of the present invention can include, but is not limited to: 21-acetoxypregnenolone, alclometasone, algestone, amcinonide, beclomethasone, betamethasone, budesonide, chloroprednisone, ciclesonide, clobetasol, clobetasone, clocortolone, cloprednol, corticosterone, cortisone, cortivazol, deflazacort, desciclesonide, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, (11b,16a)-16,17-[butylidenebisbis(oxy)]-11,21-dihydroxy-16-methyl-pregna-1,4-diene-3,20-dione 21-[(4'-nitrooxymethyl) benzoate] and derivatives, analogues, enantiomer forms, stereoisomers, anhydrides, acid addition salts, base salts, solvates, and combinations thereof. In one particular preferred variation, the selected glucocorticosteroid is budesonide.

The final morphology of the particles produced according to the present invention has been selected to help reduce the dissolution rate of the particles in the lung after administration. According to Fick's law of diffusion, the dissolution rate of ICS particles in lung fluid is dependent upon the particle surface area: the lower the surface area, the slower the dissolution rate. Decreasing the specific surface area (SSA in meters$^2$/gram) of ICS particles can be achieved by increasing the particle size (Freiwald et al. (2005) *Respiratory Research* 6:21) while minimizing creation of facets or porosity in the particle morphology. Increasing the ICS particle size may lower drug delivery efficiency since the ideal particle size for lung delivery is 1-5 microns. For next generation nebulizers the particle size should ideally be below 3 microns to ensure passage of the majority of drug particles through the mesh/membrane. This invention used the approach to tightly control particle dimension in the range less than 3 microns with a narrow particle size distribution (1-3 microns) and a low aspect ratio (less than 2), while controlling morphology to achieve a square bifrustrum shape which approaches a smooth spherical or cubical solid in having minimum possible SSA In particular, FIG. 1 shows the calculated specific surface area (SSA) of budesonide particles having a selection of different morphologies, where the representative particle dimension is about 2 microns. As can be seen, for the same representative 2 micron particle size, the sphere-, cube- and square bifrustum-shaped particles have a much lower SSA than flake- and rod-shaped particles. Therefore, spheres, cubes, and square bifrustum are the preferred particle morphologies to provide for extended lung residence time after administration.

Figure 2:
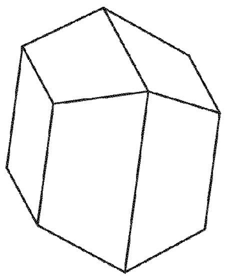
FIG. 2 depicts the morphology (crystal shape) of a square bifrustum-shaped glucocorticosteroid particle according to the present invention.
Figure 3A:
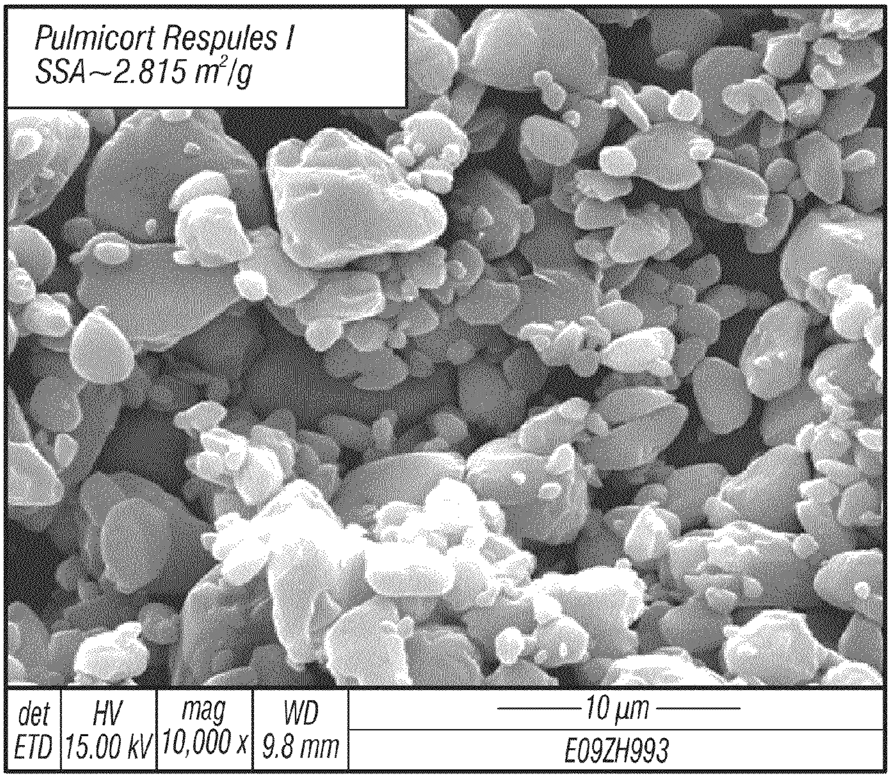
FIG. 3 depicts scanning electron microscope (SEM) images and SSA values for various budesonide particles that were tested for dissolution rate in Example 3.
Figure 3B:
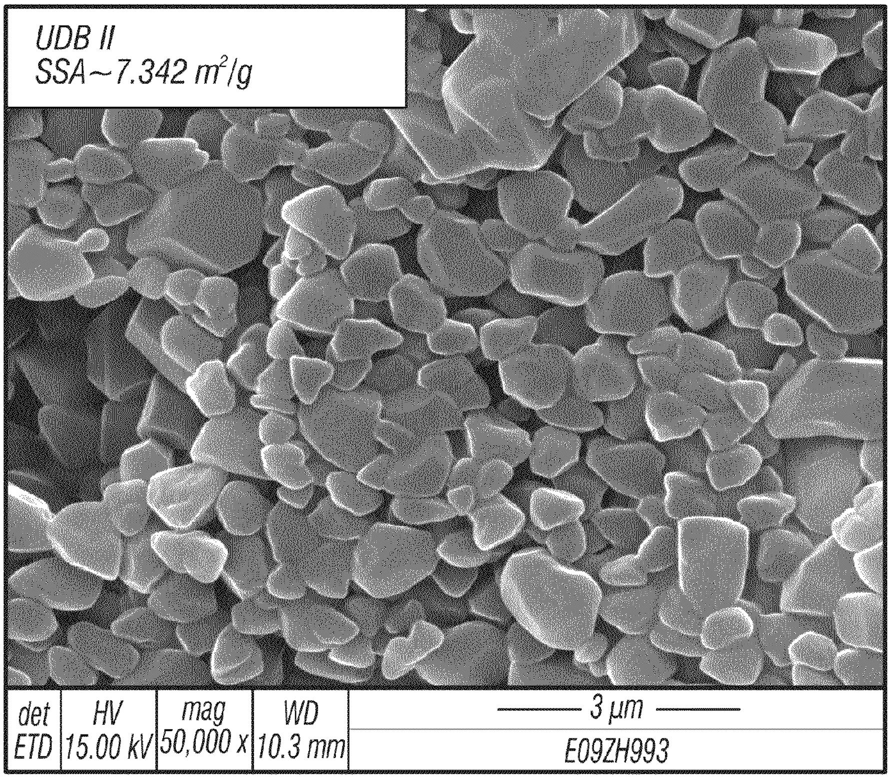
Figure 3C:
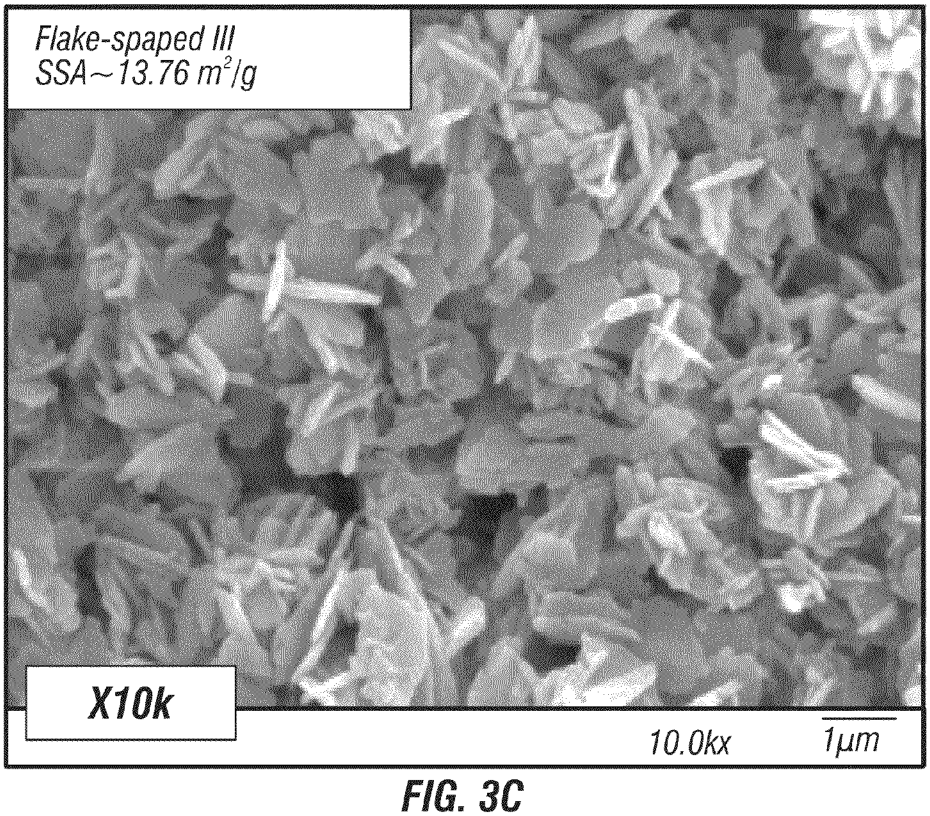
Figure 3D:
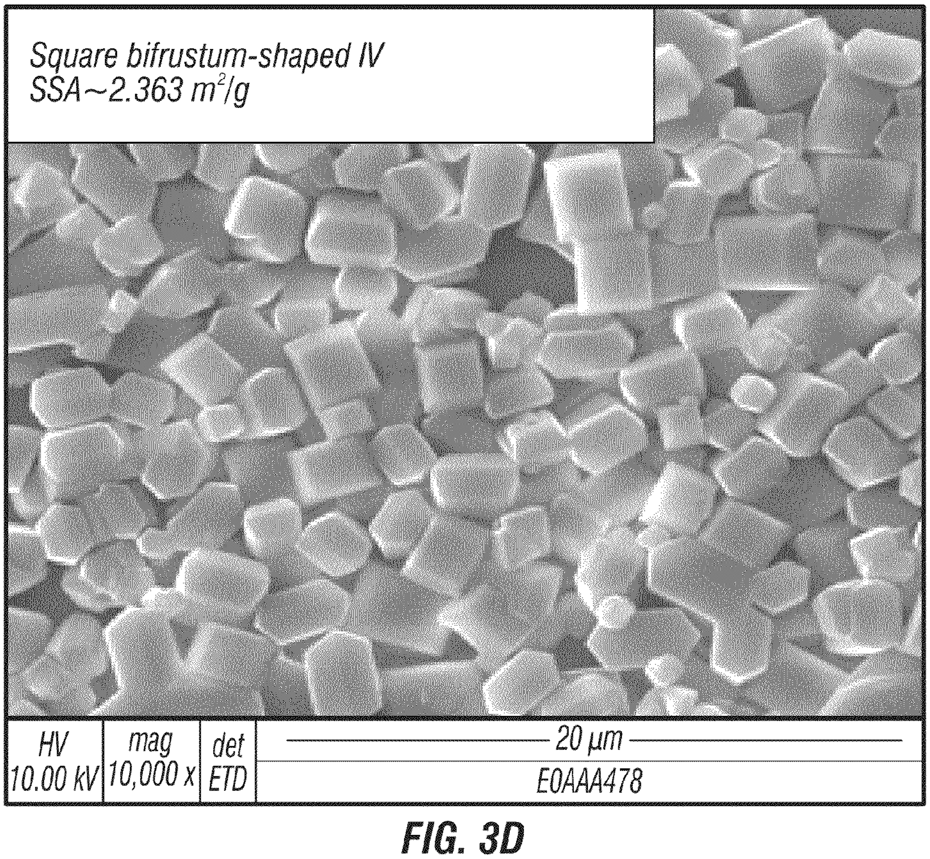
Figure 3E:
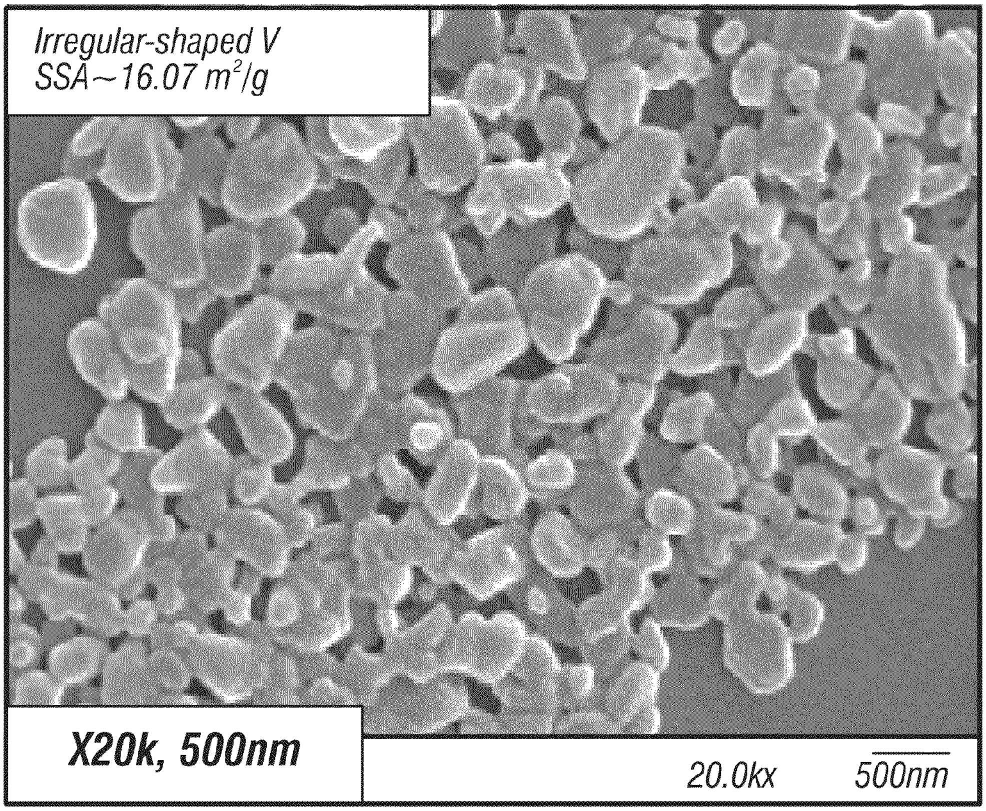
Figure 3F:
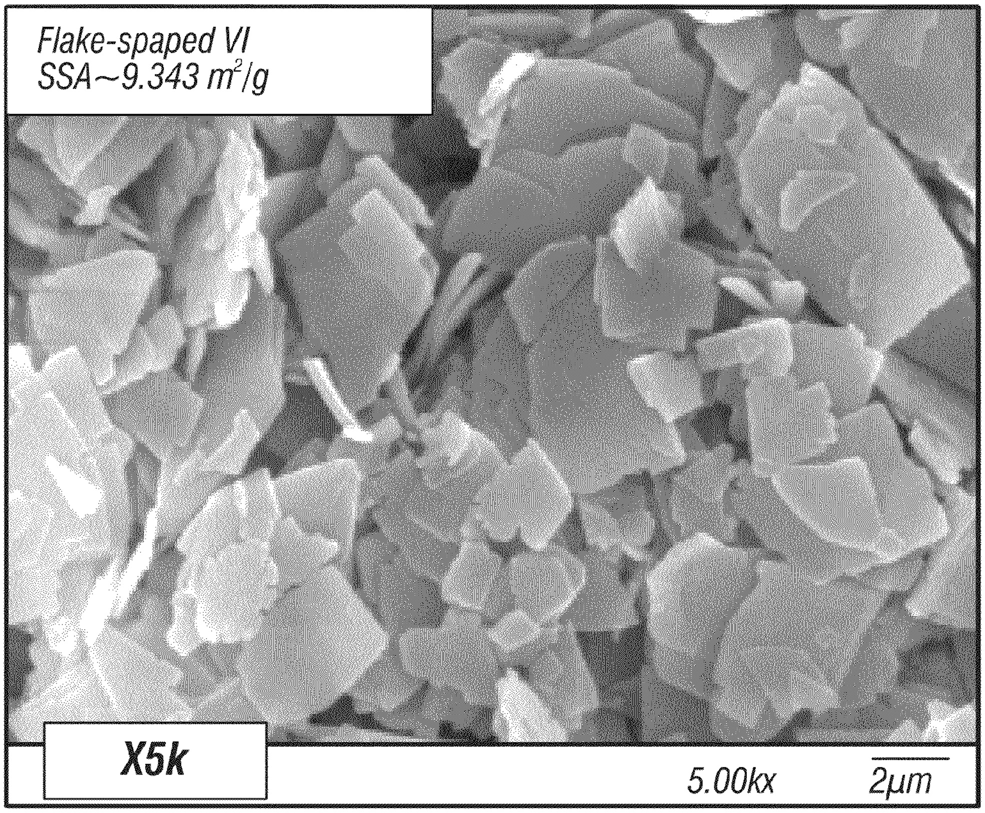

The specific surface area of square bifrustum crystals is close to that of cube and sphere and much lower than flakes and rods. Accordingly, for budesonide particles produced according to the present invention, it is preferred that the final particle morphology is square bifrustum as depicted in FIG. 2. In particular, the square bifrustum-shaped budesonide particles with a mean diameter of about 2 microns have a SSA of about 2.363 m$^2$/gram when measured by BET nitrogen absorption as shown in FIG. 3. This measured SSA matches very well with the calculated value from FIG. 1.

Figure 5A:
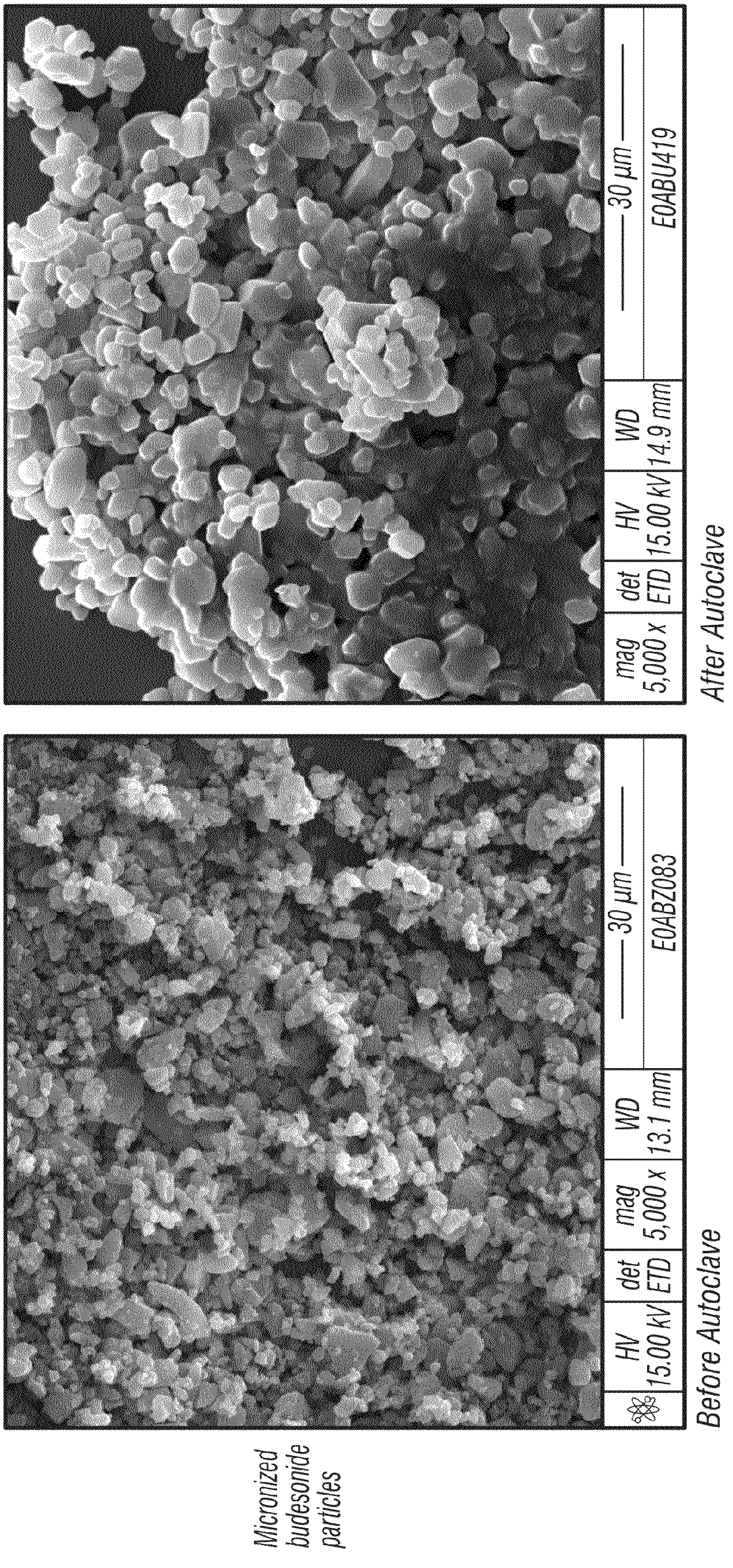
FIG. 5 shows the SEM images of budesonide particles before and after autoclave sterilization, where FIG. 5(*a*) shows images of micronized budesonide particles.
Figure 5B:
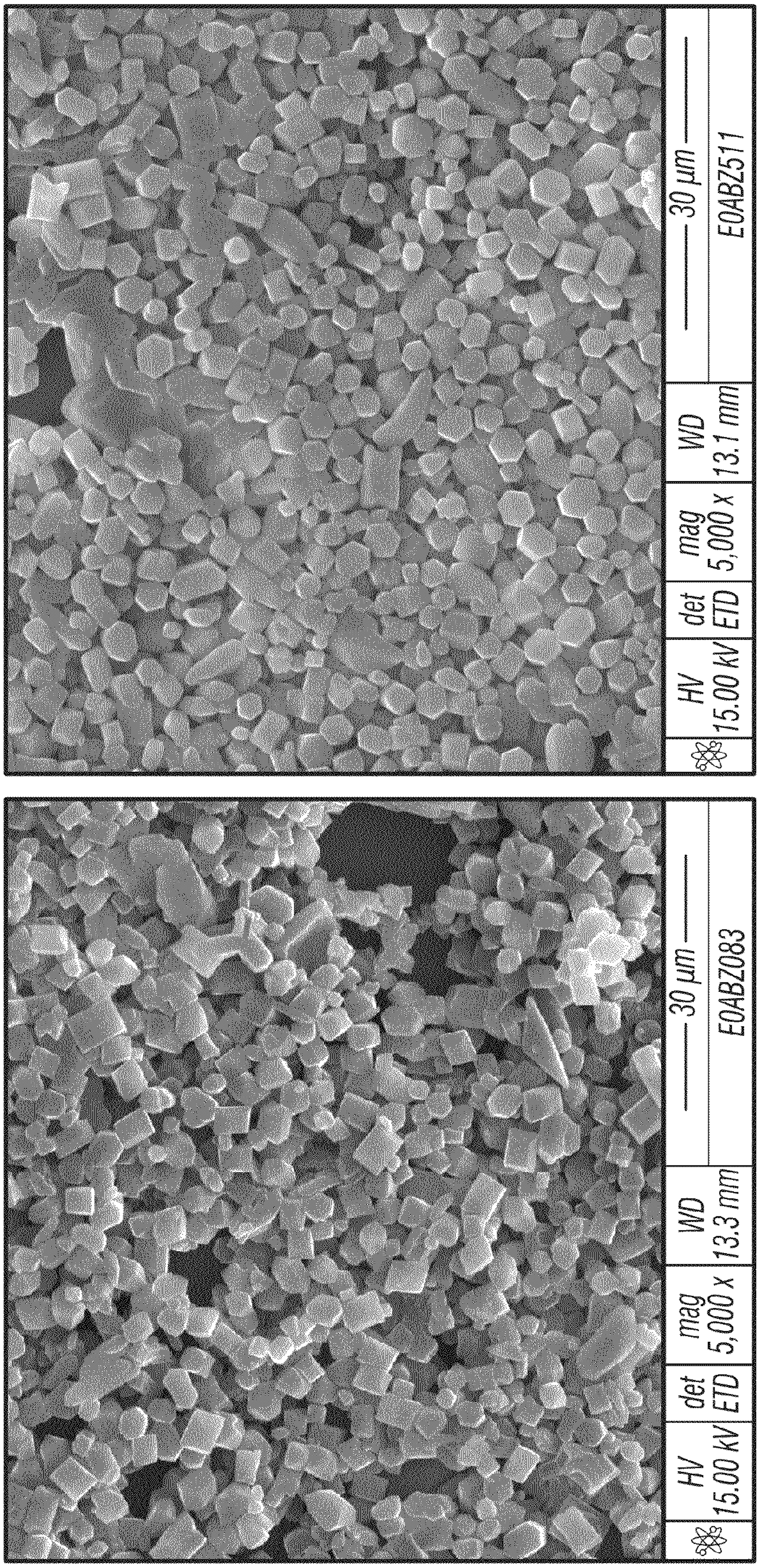
Figure 6A:
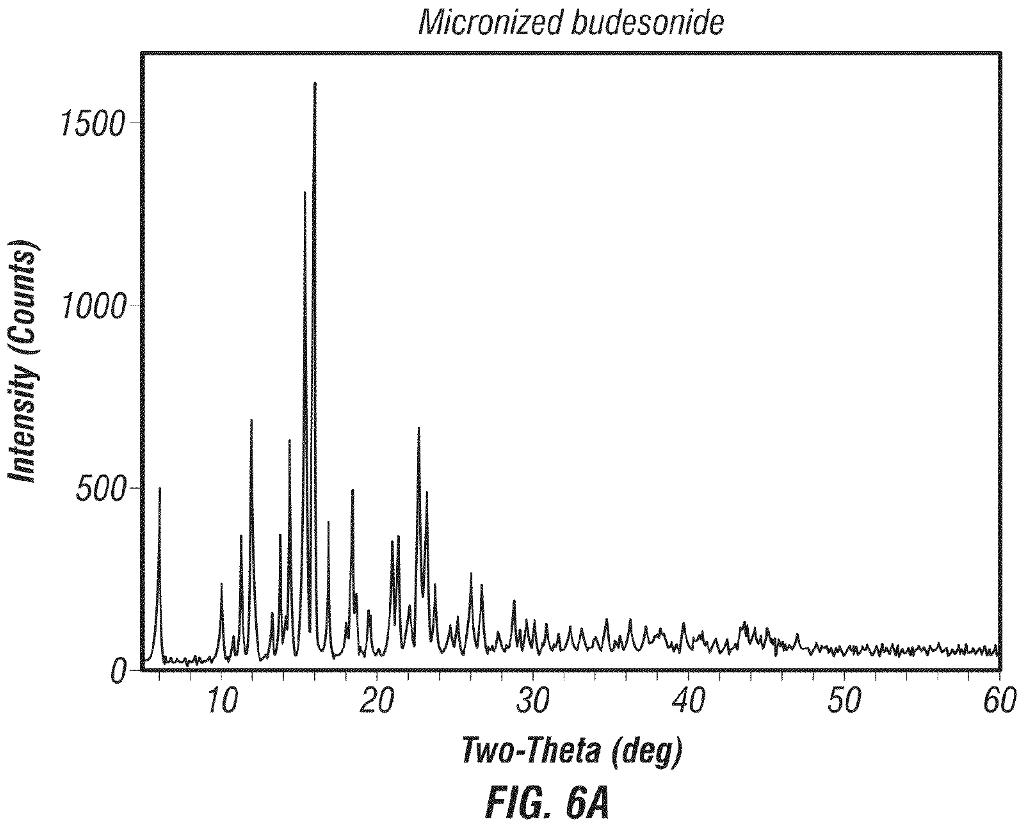
FIG. 6 shows the XRD pattern of budesonide particles where FIG. 6(*a*) shows the XRD pattern of micronized budesonide particles, and FIG. 6(*b*) shows the XRD pattern of square bifrustum-shaped budesonide particles.
Figure 6B:
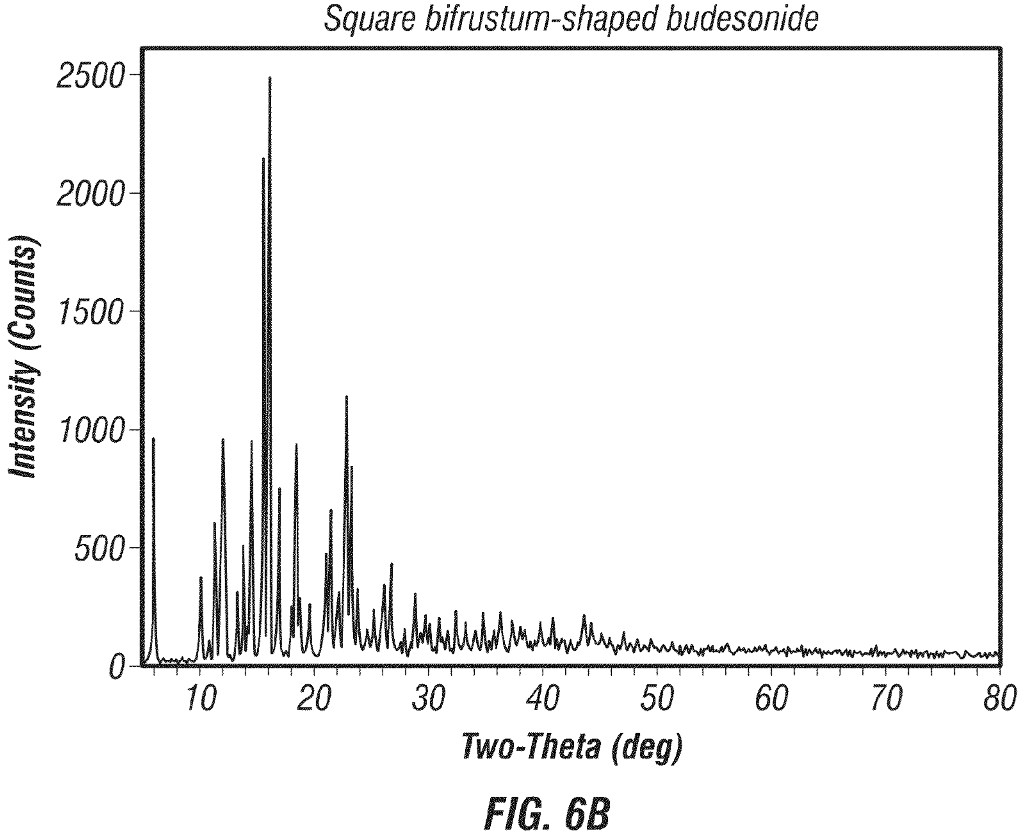

In order to enhance the physical stability of the ICS suspension formulations, it is preferred to keep the surface energy of the ICS particles as low as possible so as to minimize the Ostwald ripening in the formulation. FIG. 5 shows the SEM images of the budesonide particles before and after autoclave sterilization. (a) micronized budesonide; (b) budesonide with square bifrustum shape. The particle size of micronized budesonide particles is increased significantly after autoclave sterilization while the square bifrustum-shaped particles shows little change before and after the autoclave process. The XRD pattern of the two budesonide particles (micronized and square bifrustum-shaped) show no crystallinity difference between the two budesonide compositions (as seen in FIG. 6). This is a good indication that the square bifrustum-shaped budesonide has a surface energy low enough to minimize the Ostwald ripening while this is not true for micronized budesonide.

Budesonide particles, having a final morphology that is square bifrustum crystals, can be produced in accordance with the instant invention using a novel non-supercritical solvent/anti-solvent technique. In a typical solvent/antisolvent process for producing drug particles, the drug is dissolved in a solvent to form a solution. The solution is then mixed with an antisolvent which is miscible with the solvent. In the method of the present invention, the solvent is a co-solvent system formed from a mixture of a primary, water-miscible solvent and a secondary solvent that is partially water-soluble. The primary solvent can be any solvent that is water miscible. Suitable primary solvents include, but are not limited to, acetone, acetonitrile, methanol, ethanol, isopropanol, dimethyl sulfoxide, or mixtures thereof, with methanol being the preferred primary solvent. The primary water miscible solvent can be present in the co-solvent system at about 10 to about 90% by volume, preferably about 50% by volume. The secondary solvent in the co-solvent system can be any solvent which is miscible in the primary solvent and partially water-miscible. Suitable secondary solvents include, but are not limited to ethyl acetate, isopropyl acetate, diethyl ether, dichloromethane, methyl ethyl ketone, methyl isobutyl ketone, and any mixture thereof, with ethyl acetate being the preferred partially water miscible secondary solvent. As used herein, if a solvent is "partially water-miscible" if that solvent has a solubility in water at 20° C. of about 10 grams/liter to about 300 grams/liter. The water solubility of the exemplary secondary solvents listed above are:

| | |
|---|---|
| ethyl acetate | 83 grams/liter |
| isopropyl acetate | 43 grams/liter |
| diethyl ether | 69 grams/liter |
| dichloromethane | 13 grams/liter |
| methyl ethyl ketone | 275 grams/liter |
| methyl isobutyl ketone | 19 grams/liter. |

The secondary partially water-miscible solvent can be present in the co-solvent system at about 10 to about 90% by volume, preferably about 50% by volume.

Proceeding with the method of the invention, the budesonide drug is dissolved in the co-solvent system to form a budesonide solution. The budesonide solution is then added to an antisolvent and agitated to produce particles of budesonide. The antisolvent is formed as an aqueous solution of a dispersion enhancer, wherein a concentration of about 0.01 to 5 wt % of a dispersion enhancer is added to the water. The antisolvent may optional further include one or more of a buffering agent (e.g., sodium citrate, citric acid), an isotonicity agent (e.g., sodium chloride), and an antidoxidant (e.g., EDTA). As used herein, the term "dispersion enhancer" refers to a pharmaceutical excipient that reduces, minimizes or eliminates aggregation or agglomeration of particles of a drug in a drug suspension. Suitable dispersion enhancers include, but are not limited to, Polysorbate 20, Polysorbate 40, Polysorbate 60, Polysorbate 80, polyethylene glycol, poloxamer, or mixtures thereof. A particularly preferred dispersion enhancer is Polysorbate 80. The temperature of the antisolvent when it is combined with the solution may be in the range of about −10° C. to 50° C. with the preferable temperature being about 5° C. Agitation of the budesonide solution and antisolvent can be carried out using standard mixing techniques. In particular, the mixing can be carried out under conditions of high shear or high pressure, using a rotor-stator or high-pressure homogenizer apparatus. The final morphology of particles obtained using the method of the present invention can be controlled by varying the ratio of the water-miscible to partially water-miscible solvents in the co-solvent system, the concentration of the glucocorticosteroid in the solvent, the precipitation temperature and/or the ratio of solvent to antisolvent used in the precipitation step. In addition, control over the agitation time, as well as the amount of shear/pressure used during mixing allows for tight control over the final particle size, resulting in a particle population that has a narrow size distribution and uniform particle morphology (square bifrustum particles are obtained in the size range of about 2 microns). Accordingly, the method of the invention provides a simplified, reproducible and scalable particle formation process that can produce glucocorticosteroid particles having a narrow particle size and shape distribution, a low aspect ratio, uniform particle morphology and a reduced SSA.

In some cases, it will be necessary to practice the particle formation method of the present invention under sterile or aseptic processing conditions. This is particularly important where terminal sterilization techniques such as irradiation or steam sterilization are not feasible or contra-indicated when heat treatment can alter the physicochemical stability, ie, the particle size or the chemical composition or the corticosteroid material. Accordingly, the method of the invention can be carried out in a suitable HEPA filtered environment, either under a containment hood or in a Class 1,000 or Class 100 laboratory space. The containers that are used in the method can be sterilized using standard steam-in-place technique, and all of the solvent/antisolvent materials can be sterile-filtered using a 0.20-0.45 micron filter apparatus.

Once the glucocorticosteroid particles of the present invention have been formed and subjected to any post formation particle processing steps to provide a bulk particulate drug composition, the bulk particles are converted into an appropriate ICS aerosol formulation, for example by forming a suspension of the particles in an appropriate buffering solution such as sterile citrate-buffered isotonic saline solution.

The ICS aerosol formulations may include excipients and/or additives. Suitable excipients and/or additives that may be employed include one or more buffering agents, isotonicity agents, dispersion enhances and antioxidants.

Useful dispersion enhancers include, but are not limited to, non-ionic surface stabilizers such as polyoxyethylene sorbitan esters and Polysorbate 80. The concentrations of these excipients must be limited to a maximum level of 5 wt % to avoid the dissolution of the corticosteroid particles.

To prevent oxidative degradation of the corticosteroid or the excipients, ethylenediaminetetraacetic acid (EDTA) or a salt thereof, such as the disodium salt, citric acid, and the salts thereof can be added. Other antioxidants include, but are not limited to, vitamins, provitamins, ascorbic acid, vitamin E, or salts or esters thereof.

Other excipients that may be used in the aerosol formulations include, but are not limited to pH buffers, tonicity modifiers.

Exemplary ICS budesonide suspension formulations that may be produced in accordance with the present invention may include square bifrustum-shaped budesonide particles and one or more of a dispersion enhancer, and EDTA, pH and tonicity modifiers. In some variations, the formulations include the budesonide particles, Polysorbate 80, and EDTA. For example, the formulations may comprise between about 0.005% to about 0.1% by weight budesonide particles, between about 0.0001% to about 1.0% by weight Polysorbate 80, and between about 0.0001% to about 5.0% by weight EDTA. In one variation, the formulation includes about 0.005% by weight EDTA. Exemplary budesonide formulations are shown below in Table 1.

TABLE 1

Exemplary Budesonide Formulations

| Component | Concentration |
|---|---|
| Budesonide | 200 μg/ml |
| Polysorbate 80 | 125 μg/ml |
| NaCl | 8.5 mg/ml |
| EDTA (Edetate Disodium Dihydrate) | 50 μg/ml |
| Sodium Citrate Dihydrate | 0.624 mg/ml |
| Citric Acid | 0.188 mg/ml |
| Water for Injection | q.s. to 0.5 ml |

The square bifrustum-shaped particles used in these formulations may be made by dissolving the drug compound in cosolvent. The cosolvent can comprise a water-miscible solvent, a partially water-miscible solvent or both a water-miscible solvent and a partially water miscible solvent. Suitable water-miscible solvents include, but are not limited to, acetone, acetonitrile, methanol, ethanol, isopropanol, dimethyl sulfoxide, or mixtures of any of the foregoing solvents. Suitable partially water-miscible solvents include, but are not limited to, ethyl acetate, isopropyl acetate, n-butyl acetate, diethyl ether, t-butyl methyl ether, chloroform, dichloromethane, methyl ethyl ketone, methyl isobutyl ketone, or mixtures of any of the foregoing solvents. In a non-limiting example, Example 1 describes a method of producing square bifrustum-shaped budesonide particles dissolved in a mixture of methanol and ethyl acetate. The solvent mixture is then combined with an antisolvent to produce the desired particles.

The above described methods can also be performed on a continuous or semi-continuous process, and therefore gives the added advantage of scalability. The solvent/antisolvent streams can be fed into an agitator on a continuous or semi-continuous basis. Examples of suitable agitators generating conditions of high shear or high pressure (or both) include a rotor-stator or high-pressure homogenizer apparatus. Example 2 below describes square bifrustum-shaped budesonide particles using this technique.

Once formulated, the ICS budesonide suspension formulations produced according to the present invention can be dosed into any suitable individual unit dose container including, for example, blisters, vials, ampoules, canisters, cartridges, and the like. The individual containers may be made from any suitable material that does not react with the formulation, and which does not allow substantial permeation of oxygen through the container wall. Accordingly, glass may be used but, in a preferred variation, a polymer material is used. For example, thermoplastic polymers such as polycarbonate, polyethylene, including low density polyethylene (LDPE), polyester, polystyrene, polypropylene, polysulfone, polyurethane, ethylene-vinyl-acetate, and the like, may be used. The materials may be transparent, translucent, or colored. In some variations, different materials may be employed to make different parts of the containers. For example, the cap, body, and identifier portions of the container may be made from different polymers. In one preferred variation, the ICS budesonide suspension formulations produced according to the present invention can be dosed into an ampoule substantially similar to that described in U.S. Pat. No. 7,032,590. The individual unit dose containers described herein can include sufficient formulation to administer the glucocorticosteroid at least once a day. However, administration of some drugs may be repeated or administered on a more frequent basis. The dose of the glucocorticosteroid may also vary, but will generally be a low dose. For example, when budesonide particles are used, the total dose of budesonide that is administered in the formulation may be less than about 0.30 mg. In one variation, the budesonide dose is between about 0.22 mg to about 0.27 mg. In another variation, the budesonide dose is between about 0.10 mg to about 0.27 mg. In other variations, the dose of budesonide is about 0.25 mg or less. In still further variations, the dose of budesonide is about 0.135 mg or less.

The ICS budesonide suspension formulations produced according to the present invention can be administered using any suitable nebulizer device to generate the aerosol of glucocorticosteroid for administration. Examples of commercially available nebulizers include the AERONEB™ and AERONEB GO™ nebulizers (Aerogen, San Francisco, Calif.); PARI nebulizers, including the PARI LC PLUS™, PARI BOY™ N, PARI eflow, PARI LC SINUS, PARI SINUSTAR™, PARI SINUNEB, and PARI DURANEB™ nebulizers (PARI Respiratory Equipment, Inc., Monterey, Calif.); MICROAIR™ nebulizer (Omron Healthcare, Inc, Vernon Hills, Ill.); HALOLITE™ nebulizer (Profile Therapeutics Inc., Boston, Mass.); RESPIMAT™ nebulizer (Boehringer Ingelheim Ingelheim, Germany); ERODOSE™ nebulizer (Aerogen, Inc., Mountain View, Calif.); OMRON ELITE™ (Omron Healthcare, Inc., Vernon Hills, Ill.); OMRON MICROAIR™ (Omron Healthcare, Inc, Vernon Hills, Ill.); MABISMIST™ II nebulizer (Mabis Healthcare, Inc, Lake Forest, Ill.); LUMISCOPE™ 6610 nebulizer; (The Lumiscope Company, Inc., East Brunswick, N.J.); AIRSEP MYSTIQUE™ nebulizer, (AirSep Corporation, Buffalo, N.Y.); ACORN-1 and ACORN-11 (Vital Signs, Inc, Totowa, N.J.); AQUATOWER™ nebulizer (Medical Industries America, Adel, Iowa); AVA-NEB (Hudson Respiratory Care Incorporated, Temecula, Calif.); AEROCURRENT™ nebulizer utilizing the AEROCELL™ disposable cartridge (AerovectRx Corporation, Atlanta, Ga.); CIRRUS (Intersurgical Incorporated, Liverpool, N.Y.); DART (Professional Medical Products, Greenwood, S.C.); DEVILBISS™ PULMO AIDE (DeVilbiss Corp; Somerset, Pa.); DOWNDRAFT™ (Marquest, Englewood, Colo.); FAN JET (Marquest, Englewood, Colo.); MB-5 (Mefar, Bovezzo, Italy); MISTY NEB™ (Baxter, Valencia, Calif.); SALTER 8900 (Salter Labs, Arvin, Calif.); SIDESTREAM™ (Medic-Aid, Sussex, UK); UPDRAFT-II™ (Hudson Respiratory Care; Temecula, Calif.); WHISPER JET™ (Marquest Medical Products, Englewood, Colo.); AIOLOS™ (Aiolos Medicnnsk Teknik, Karlstad, Sweden); INSPIRON™ (Intertech Resources, Inc., Bannockburn, Ill.); OPTIMIST™ (Unomedical Inc., McAllen, Tex.); PRODOMO™ and SPIRA™ (Respiratory Care Center, Hameenlinna, Finland); AERx™, Essence™, and Ultra™ nebulizers (Aradigm Corporation, Hayward, Calif.); SONIK™ LDI Nebulizer (Evit Labs, Sacramento, Calif.); and SWIRLER® Radioaerosol System (AMICI, Inc., Spring City, Pa.). Exemplary vibrating membrane, mesh or plate nebulizers are described by R. Dhand (Respiratory Care, (December 2002), 47(12), p. 1406-1418). Particularly preferred devices for use in the practice of the invention are next generation nebulizers such as to the AERx™ and Essence™ devices (Aradigm Coorp., Hayward, Calif.), the PARI eFlow device (PARI Respiratory Equipment, Monterey, Calif.), the TouchSpray device (The Technology Partnership, Cambridge, UK), the Ineb and Myneb devices (Respironic, Andover, Mass.), the MicroAir device (Omron Healthcare, Inc., Vernon Hills, Ill.) and the AERONEB™ and AERONEB GO™ devices (Aerogen, San Francisco, Calif.). The AERONEB devices, and various components thereof are described in U.S. Pat. Nos. 5,758,637; 5,938,117; 6,085,740; 6,235,177; 6,467,476; 6,554,201; 6,915,962 and 7,066,398.

ICS suspension formulations described herein may be used to treat patients with various respiratory conditions. As used herein, the terms "treatment or treating" refer to the amelioration, reduction, or prevention of symptoms indicative of a respiratory condition. For example, the methods may be used to treat inflammatory airway conditions such as asthma, chronic obstructive pulmonary disease (COPD), Respiratory Distress Syndrome, chronic cough, and bronchiolitis. Infectious and neoplastic airway conditions are also contemplated. The patients that may be treated can be of any age, ranging from neonates, infants, children, and adolescents (pediatric age groups). The formulations are useful in adult patients.

When considering the effectiveness of delivery of ICS suspension formulations using a nebulizer, a major factor governing the effectiveness of drug deposition in the lungs is the size and shape of the inspired particles. Depending on the particle size, total deposition in various regions of the lung may vary from 11% to 98%. Heyder et al. (1986) *Aerosol Sci.* 17:811-825. Therefore, proper selection of particle size and morphology using the methods of the present invention provides a way to target liquid droplets to a desired lung region. One parameter that may be used to define droplet size is the respirable fraction (RF). The respirable fraction (RF) of an aerosol formulation can be defined as the fraction of the mass of aerosol droplets falling between a particular size range, usually in the range from about 1 to 6 microns. Another parameter that may be used to evaluate nebulization performance is the efficiency (E). The efficiency (E) of a nebulizer is the amount of a suspension formulation which is actually aerosolized and leaves the nebulizer in aerosolized form as compared to the amount of formulation that is initially supplied to the nebulizer. Still another parameter that may be used to measure the performance of nebulizers is the delivery percentage (D) which is the respirable fraction (RF) multiplied by the efficiency (E). Most commercially available inhalers produce sprays having a respirable fraction (RF) of 80% or less, with ultrasonic nebulizers usually having a respirable fraction (RF) of less than about 50%, thereby making dosing control difficult and inaccurate. Cipolla, et al. (1994) *S.T.P. Pharma Sciences* 4(1):50-62. Such inefficiency often results from the construction of the nebulizer since a certain amount cannot be nebulized and remains within the device. Accordingly, use of the ICH particles of the present invention in aerosol formulations for delivery with both conventional nebulizers and next generation nebulizers can help increase the delivery percentage (D) performance of the nebulizer device. In some cases, where a next generation nebulizer is used, the delivery percentage (D) performance can be at least about 85%, in some cases 90%, in still other cases 95% or even approaching 100%.

EXAMPLES

Example 1

Formation of Square Bifrustum-Shaped Particles

Budesonide (0.1 grams) was dissolved in a mixture of methanol (5 milliliters) and ethyl acetate (5 milliliters). The budesonide solution was then added to 80 milliliters of a solution of Polysorbate 80 (0.05 w/v %) in $H_2O$ at a temperature of 5° C. with strong agitation by a rotor-stator homogenizer. Agitation was applied for about 5 minutes. The majority of the particles obtained by the process were square bifrustum-shaped and were in the size range of 1-3 microns and predominately about 2.5 microns.

Budesonide (0.1 grams) was dissolved in a mixture of methanol (4 milliliters) and ethyl acetate (6 milliliters). The budesonide solution was then added to 80 milliliters of a solution of Polysorbate 80 (0.05 w/v %) in $H_2O$ at a temperature of 5° C. with strong agitation by a rotor-stator homogenizer. Agitation was applied for about 5 minutes. The majority of the particles obtained by the process were square bifrustum-shaped and were in the size range of 1-3 microns and predominately about 2.5 microns.

Though a rotor-stator homogenizer was used to provide agitation in, other mechanical means can be used such as a high pressure homogenizer or an ultrasonic homogenizer.

Example 2

Formation of Square Bifrustum-Shaped Particles

Fresh antisolvent and solution were supplied directly to the homogenizer. The mixture was spun out of the homogenizer into air, minimizing the antisolvent concentration in the mixture. Specifically, a 5% budesonide solution in 50/50 (v/v) methanol/ethyl acetate was injected into a 5% Tween-80 (polysorbate 80) water solution stream (antisolvent). The two streams were directly fed into a homogenizer. The liquid was spun out of the homogenizer and was collected by a collection device. Square bifrustum-shaped budesonide particles were formed.

A 1% budesonide solution in 70/30 (v/v) methanol/ethyl acetate was injected into a 0.5% Tween-80 water solution stream. The two streams were directly fed into a homogenizer. The liquid that was spun out of the homogenizer was collected by a collection device. Square bifrustum-shaped budesonide particles were formed.

Additional experiments using an antisolvent solution of 0.05% (w/v %) Tween-80 water solution containing ethyl acetate were also performed. A 1% budesonide solution in 60/40 (v/v) methanol/ethyl acetate was added to 80 mL of 0.05% (w/v %) Tween-80 water solution containing $1/40^{th}$ part of ethyl acetate in an ice water bath under strong agitation (approximately 17,500 rpm) by a rotor-stator homogenizer. Square bifrustum shaped budesonide particles were formed. A 1% budesonide solution in 70/30 (v/v) methanol/ethyl acetate was added into 80 mL of 0.05% (w/v %) Tween-80 water solution containing $1/40^{th}$ part ethyl acetate in an ice water bath, under strong agitation by a rotor-stator homogenizer. Square bifrustum-shaped budesonide particles were formed.

Example 3

Dissolution Testing of Exemplary Budesonide Particles

Particles of budesonide were tested for dissolution rate in an artificial epithelial lung fluid. The procedure was performed in a standard USP dissolution apparatus II operated at 75 rpm, in 500 milliliters of simulated epithelial lung fluid (SELF) at 37° C. under sink conditions. The formulation of SILF was as follows:

| | |
|---|---|
| magnesium chloride, hexahydrate | 0.2033 grams/liter |
| sodium chloride | 6.0193 grams/liter |
| potassium chloride | 0.2982 grams/liter |
| sodium phosphate, dibasic, anhydrous | 0.1420 grams/liter |
| sodium sulfate, anhydrous | 0.0710 grams/liter |
| calcium chloride, dihydrate | 0.3676 grams/liter |
| sodium acetate, trihydrate | 0.9526 grams/liter |
| sodium bicarbonate | 2.6043 grams/liter |
| sodium citrate, dehydrate | 0.0970 grams/liter |

The pH of the above solution is adjusted to 7.4 by addition of dilute hydrochloric acid.

The specific surface area of budesonide particles with various morphologies were tested by Brunauer-Emmett-Teller (BET) krypton adsorption at 25° C. These particles were also used in the dissolution study described below. A description of the particles and the SSA (expressed in $m^2/g$) results are as follows: (I) Pulmicort Respules (AstraZeneca LP, Wilmington, Del. 19850), irregular-shaped budesonide particles produced by traditional micronization technique, SSA: 2.82 $m^2/g$ (SEM image 3a); (II) UDB (Elan), irregular-shaped budesonide particles produced using wet-milling technique, SSA: 7.34 $m^2/g$ (SEM image 3b); (III) flake-shaped budesonide particles produced using a solvent/antisolvent precipitation technique, SSA: 13.76 $m^2/g$ (SEM image 3c); (IV) square bifrustum-shaped budesonide particles produced using the method of Example 1 above, SSA: 2.36 $m^2/g$ (SEM image 3d); (V) irregular-shaped budesonide particles produced using a high pressure homogenization milling technique, SSA: 16.07 $m^2/g$ (SEM image 3e); and (VI) flake-shaped budesonide particles produced using a solvent/antisolvent precipitation technique. SSA: 9.34 $m^2/g$ (SEM image 3f). Scanning electron microscope images of the budesonide particles are provided in FIG. 3.

Figure 4:
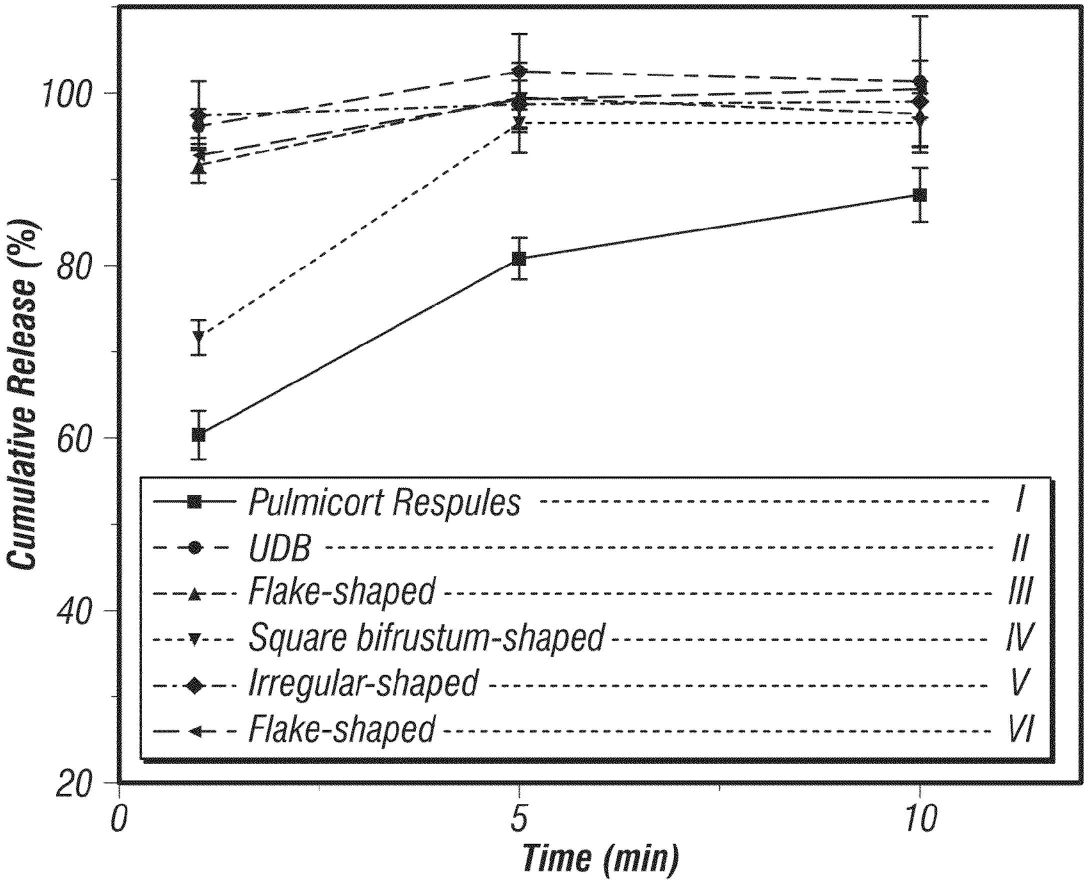
FIG. 4 is a graphical representation of the dissolution rate data obtained in Example 3, where the dissolution rate of square bifrustum budesonide crystals produced according to the methods of the instant invention was compared against the dissolution rates of other budesonide crystal morphologies.

The dissolution test results are depicted in FIG. 4. As can be seen, the trace for particle sample (IV), (-▼-), shows the dissolution curve for the particle morphology of the instant invention which is a square bifrustum shape. The test procedure shows a cumulative release of less than about 85% at 1 minute and a cumulative release of less than about 95% at 5 minutes.

When compared to the dissolution rate of the other particles tested, the square bifrustum-shaped particle sample (IV) is solubilized slower relative to the particle samples (II), (III), (V) and (VI) because it has a lower specific surface area. If a long acting formulation is required, then particles of the instant invention which have a low specific surface area (e.g. a square bifrustum shape) can be utilized, because it will take a relatively longer period of time for the same mass to dissolve in the lung fluid, whereas particles which have a relatively high specific surface area (e.g. flakes or rods) would dissolve much quicker.

Example 4

Autoclave Sterilization of Micronized Budesonide Particles

Micronized budesonide particles were suspended in a solution of Polysorbate 80 (0.5 w/v %) in $H_2O$ at the concentration of 5 w/v %. The obtained budesonide slurry was subjected to autoclave sterilization at 121° C. for 30 min. The SEM images of the micronized particles before and after autoclave sterilization are shown in FIG. 5(*a*). As can be seen, the micronized particles were agglomerated after the autoclaving process, and the individual particles had a significantly increased final particle size (from sub-micron size to about 1-5 microns after autoclaving).

Example 5

Autoclave Sterilization of Square Bifrustum-Shaped Budesonide Particles

Square bifrustum-shaped budesonide particles were suspended in a solution of Polysorbate 80 (0.5 w/v %) in $H_2O$ at the concentration of 5 w/v %. The obtained budesonide slurry was subjected to autoclave sterilization at 121° C. for 30 min. The SEM images of the square bifrustum-shaped particles before and after autoclave sterilization are shown in FIG. 5(*b*). As can be seen, the square bifrustum-shaped particles did not agglomerate after autoclaving, and retained their original size and morphology.

Example 6

Pharmacokinetic Evaluation of Budesonide Particle Formulations

Budesonide is a relatively fast-dissolving glucocorticosteroid (Talton et al. (2000) *"Nano-thin coatings for improved lung targeting of glucocorticoid dry powders"*, Respiratory Drug Delivery VII, May 14-18, 2000, Florida) with a rapid absorption from the lung in both humans and animals. However, despite such rapid absorption kinetics, some inhaled budesonide particle formulations have been shown effective in once-daily treatment in patients with asthma and rhinitis (see, e.g., Brogden et al. (1992) *Drugs* 44:375-407 and Campbell, L M (1997) *Drugs* 58 (Suppl 4):25-33), and budesonide currently is the only inhaled steroid approved for once-daily treatment of mild to moderate asthma (see label for Pulmicort Respules®, AstraZeneca LP, Wilmington, Del. 19850). It is a theory of the present invention that certain glucocorticoid particle morphologies can extend lung residence time of small sized particles after administration and thereby provide for extended release kinetics. Accordingly, the following pharmacokinetic (pK) study was carried out in order to compare lung residence time after administration between suspension formulations containing: (a) micronized budesonide particles; (b) budesonide particles with flake or spindle shapes; (c) square bifrustum-shaped particles produced according to the present invention; (d) irregular-shaped particles made by wet milling; and (e) a commercially available, long-acting budesonide (irregularly shaped) particle suspension (Pulmicort Respules).

(Study Objectives)

Seven budesonide formulations were assessed for the ability to cross the lung by perfusion on an isolated lung perfusion system. LC-MS/MS was utilized to measure budesonide concentration in perfusate samples collected for up to approximately 123 minutes after intratracheal (IT) administration of the representative formulations to male Sprague-Dawley rats. The mass of budesonide remaining in the lung was also measured at the terminus of the procedure.

The isolated perfused lung model is ideally suited for pK studies of inhaled compounds because it allows for very frequent sampling and avoids the problem of recirculation of blood from peripheral vascular beds. Sprague-Dawley rats were selected for this study because they are an outbred strain and the strain most often used in the isolated perfused lung model. This study was designed to provide lung retention time and pharmacokinetic data that would aid in determining which study formulation may provide the most optimal characteristics for the treatment of asthma.

(Animal Subjects)

The animal subjects were male Sprague-Dawley rats (aged 9-10 weeks with 300-400 g body weight at start of study), uniquely identified by tail tattoo, microchip or ear tag in addition to cage cards. Study animals were housed in standard cages and quarantined for a period of two weeks to observe signs of clinical illness, and were fed ad libitum with unlimited access to water and keep in a standard animal environment and photoperiod. The study complied with all applicable sections of the Final Rules of the Animal Welfare Act Regulations (9 CFR Parts 1, 2 and 3) and the Guide for the Care and Use of Laboratory Animals National Research Council, National Academy Press, Washington, D.C., Copyright 1996.

(Isolated Perfused Lung Setup)

After release from quarantine, the study animals were euthanized with an IP injection of a barbiturate (minimum 150 mg/kg pentobarbital). The trachea, pulmonary artery and left ventricle were cannulated and the heart/lung bloc was removed from the thoracic cavity. The heart/lung bloc was placed in an artificial thoracic cavity (Hugo Sachs Electronik-Harvard). The budesonide suspension test formulations were administered by intratracheal installation at a volume of 40-100 μL. Following test formulation delivery, fractionated single pass perfusate samples were collected over a 2 hour period. The concentration of budesonide in the perfusate and lung tissue was determined by Liquid Chromatography-Mass Spectrometry (LC-MS/MS).

(Test Formulations)

All test formulations were aqueous budesonide particle suspensions and were produced or obtained as follows. Budesonide particles for the Group-1 formulation were produced by micronization (micronized) to provide a sub-micron sized particle population having irregular shapes which was then autoclaved using the process of Example 4. The final particle size range was from about 1 to 5 microns. The micronized/autoclaved particles were suspended in the aqueous suspension medium described in Table 1 above (aqueous medium containing Polysorbate 80, NaCl, EDTA, Sodium Citrate Dihydrate, Citric Acid) to produce an aerosol formulation containing budesonide at a concentration of 0.182 mg/mL. Budesonide particles for the Group-2 formulation were produced as follows. Budseonide was dissolved in methanol at a concentration of 5 w/v %. The budesonide solution was then precipitated into water in the volume ratio of 1:8 under agitation by a rotor-stator homogenizer (Ultra-Turrax® T25) at the temperature of approximately 5° C. The budesonide particles were collected by filtration as flake-shaped particles with a size range of about 2 to microns. The flake-shaped particles were suspended in the aqueous suspension medium described in Table 1 above (aqueous medium containing Polysorbate 80, NaCl, EDTA, Sodium Citrate Dihydrate, and Citric Acid) to produce an aerosol formulation containing budesonide at a concentration of 0.189 mg/mL. Budesonide particles for the Group-3 formulation were produced as follows. Budseonide was dissolved in methanol at a concentration of 5 w/v %. The budesonide solution was then precipitated into 0.5 w/v % Polysorbate 80 solution in the volume ratio of 1:8 under agitation by a rotor-stator homogenizer (Ultra-Turrax® T25) at the temperature of approximately 5° C. The budesonide particles were collected by filtration as spindle-shaped particles with a size range of about 2 to 7 microns. The spindle-shaped particles were suspended in the aqueous suspension medium described in Table 1 above (aqueous medium containing Polysorbate 80, NaCl, EDTA, Sodium Citrate Dihydrate, Citric Acid) to produce an aerosol formulation containing budesonide at a concentration of 0.203 mg/mL. Budesonide particles for the Group-4 formulation were produced using the method of Example 1. The budesonide particles were square bifrustrum-shaped and predominately had a size of about 2.5 microns with a range of from 1 to 3 microns. The square bifrustum-shaped particles were suspended in the aqueous suspension medium described in Table 1 above (aqueous medium containing Polysorbate 80, NaCl, EDTA, Sodium Citrate Dihydrate, Citric Acid) to produce an aerosol formulation containing budesonide at a concentration of 0.191 mg/mL. Budesonide particles for the Group-5 formulation were produced using a wet milling technique. The particles were nanoparticles, with an irregular shape and a size range of about 200 to 800 nanometers (0.2 to 0.8 microns). The irregular-shaped particles were suspended in the aqueous suspension medium described in Table 1 above (aqueous medium containing Polysorbate 80, NaCl, EDTA, Sodium Citrate Dihydrate, Citric Acid) to produce an aerosol formulation containing budesonide at a concentration of 0.167 mg/mL. The Group-6 formulation was obtained commercially (Pulmicort Respules®, AstraZeneca). The particles in the suspension were irregular-shaped, and had a size range of about 1 to 8 microns. The particles are suspended in an aqueous suspension medium (aqueous medium containing Polysorbate 80, NaCl, EDTA, Sodium Citrate Dihydrate, Citric Acid) to produce a formulation containing budesonide at a concentration of 0.250 mg/mL. Budesonide particles for the Group-7 formulation were produced using the method of Example 1. The budesonide particles were square bifrustrum-shaped. The particles were then autoclaved using the process of Example 5. The final (autoclaved) particles maintained their square bifrustum shape and predominately had a size of about 2.5 microns with a range of from 1 to 3 microns. The square bifrustum-shaped/autoclaved particles were suspended in the aqueous suspension medium described in Table 1 above (aqueous medium containing Polysorbate 80, NaCl, EDTA, Sodium Citrate Dihydrate, Citric Acid) to produce an aerosol formulation containing budesonide at a concentration of 0.211 mg/mL.

(Dose Preparation)

The test formulations contained in single unit dose vials (1.5 ml or 2 ml) were inverted several times before being transferred to a secondary container. Bulk formulations were diluted in saline and were gently swirled, and then aliquots of 40-100 μl were drawn up in a syringe and installed IT into the isolated perfused lung model directly through a cannula placed at the top of the trachea.

Once produced, the test budesonide suspension formulations were tested in the isolated perfused lung test as set forth in Table 2 below.

TABLE 2

Isolated Perfused Lung Test Parameters

| Study Group | No. of Study Animals | Budesonide Particles | Dose Volume (μl) | Concentration (mg/ml) | Budesonide Dose (mg) |
|---|---|---|---|---|---|
| Group-1 | 3 | irregular-shaped 1 to 5 microns (autoclaved) | 100 | 0.182 | 0.018 |
| Group-2 | 3 | flake-shaped, 2 to 5 microns | 100 | 0.189 | 0.019 |
| Group-3 | 3 | spindle-shaped 2 to 7 microns | 100 | 0.203 | 0.020 |
| Group-4 | 3 | * square bifrustum-shaped, 2.5 microns | 100 | 0.191 | 0.019 |
| Group-5 | 3 | irregular-shaped, 0.200 to 0.800 microns | 60 | 0.167 | 0.010 |
| Group-6 | 3 | irregular-shaped, 1 to 8 microns | 40 | 0.250 | 0.010 |
| Group-7 | 3 | * square bifrustum-shaped, 2.5 microns (autoclaved) | 100 | 0.211 | 0.021 |

(Isolated Perfused Lung Procedure)

The Study animals were euthanized with an overdose of pentobarbital. During necropsy, the trachea and lungs were excised from the rat and placed on the IPL system cannula. The lungs were ventilated with room air at a rate of 60 breaths per minute by negative pressure ventilation. Chamber pressures were adjusted to reach target goals of a tidal volume of 2.5 ml and a peak expiratory flow of 12 ml/sec.

Single pass perfusate samples were collected over a 60-120 minute period. Perfusate samples were fractionated into 17 samples collected at approximately (min): 0.67; 1.3; 2.7; 4; 6; 8; 10; 12.5; 15; 22; 29; 36; 43; 63; 83; 103; and 123.

Perfusate and lung tissue samples were stored at −80° C. prior to subsequent analysis by LC-MS/MS. During operation of the isolated perfused lung (IPL) system pressure and flow recordings were collected using EMKA (version 2.5) software. These ancillary data were obtained to enable a cursory view of potential observations of unexpected anomalies due to specific formulations. Data was reduced to 5 minute data points for the purposes of statistical comparisons. Mean and standard error were performed on the perfusate and lung tissue concentrations using Microsoft Excel software. Pharmacokinetic properties were evaluated by WinNonlin software (Version 5.0.1, Pharsight Corporation, Sunnyvale, Calif. 94086).

(Results and Analysis)

Figure 7:
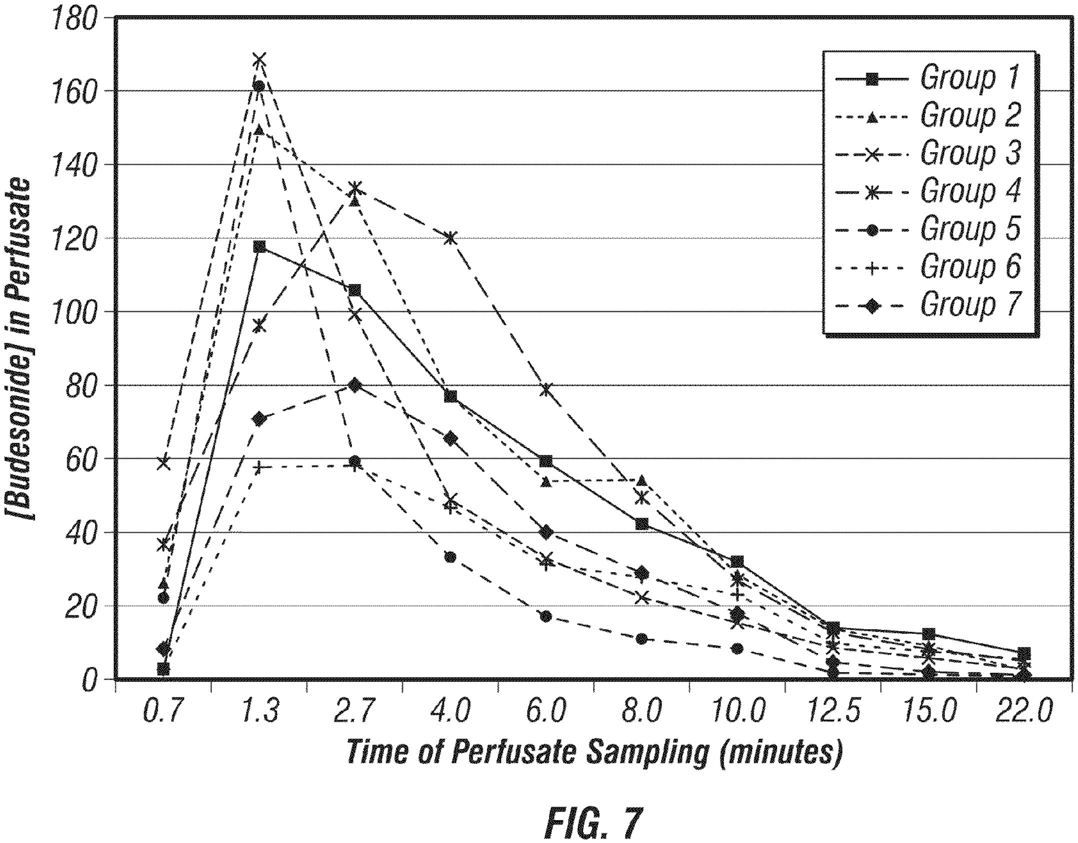
FIG. 7 depicts the pharmacokinetic parameters for the seven budesonide test formulations measured in the lung perfusate study as described in Example 6.

The concentration of budesonide at each time point for each study group (the pK parameters for budesonide formulations measured in the perfusate (ng/ml)) is reported below in Table 3 and depicted in FIG. 7.

TABLE 3 pK Parameters for Test Formulations Measured in the Perfusate (ng/ml)

| Time (min) | Group-1 | Group-2 | Group-3 | Group-4 | Group-5 | Group-6 | Group-7 |
|---|---|---|---|---|---|---|---|
| 0.7 | 2.67 | 26.4 | 58.9 | 36.6 | 22.3 | 1.1 | 7.5 |
| 1.3 | 117.6 | 149.6 | 168.6 | 96.3 | 161.4 | 57.8 | 70.7 |
| 2.7 | 106.0 | 129.9 | 99.2 | 133.3 | 59.3 | 58.2 | 80.4 |
| 4.0 | 76.9 | 77.1 | 48.8 | 120.2 | 33.2 | 46.8 | 65.4 |
| 6.0 | 59.4 | 53.8 | 32.7 | 78.8 | 17.0 | 31.4 | 39.6 |
| 8.0 | 42.3 | 54.4 | 22.1 | 49.4 | 11.0 | 27.8 | 28.9 |
| 10.0 | 31.9 | 28.5 | 15.5 | 26.9 | 8.4 | 23.0 | 18.0 |
| 12.5 | 14.0 | 13.5 | 8.4 | 12.6 | 1.9 | 9.6 | 4.5 |
| 15.0 | 12.2 | 9.0 | 5.7 | 8.0 | 1.3 | 7.5 | 2.1 |
| 22.0 | 7.3 | 2.6 | 2.9 | 4.9 | 1.0 | 5.3 | 1.2 |
| 29.0 | 6.2 | 1.6 | 1.7 | 3.2 | 0.9 | 3.8 | 1.9 |
| 36.0 | 5.4 | 0.9 | 1.8 | 2.0 | 0.8 | 3.9 | 1.5 |
| 43.0 | 4.6 | 1.6 | 1.3 | 1.7 | 0.6 | 4.1 | 1.0 |
| 63.0 | 5.0 | 0.7 | 0.9 | 2.00 | 0.5 | 3.8 | 2.3 |
| 83.0 | 4.6 | 0.6 | 1.5 | 2.44 | 0.6 | 4.6 | |
| 103.0 | 3.5 | 0.4 | 0.5 | 2.7 | 0.6 | 1.8 | |
| 123.0 | 2.1 | 1.3 | 0.2 | 2.8 | 0.7 | 1.7 | |

The distribution of the nominal dose of budesonide (the amount installed into the test system), comparing the mass of budesonide collected in perfusate vs. the mass of budesonide remaining in the lung at the end of the sampling period, is reported below in Table 4. The mass balance of the nominal dose of budesonide is also outlined. As can be seen, the Group-1, Group-4, Group-6 (Pulmicort Respules) and Group-7 results all had mass balances between 75-125% of the nominal dose of budesonide, while the Group-3 and Group-5 results had mass balances that were <50% of the nominal dose. It is highly plausible that the rapid removal of these two formulations from the lung took the samples below the limit of quantitation at later sampling time points, and that much of the budesonide that made its way into the perfusate was not quantified accurately due to the sensitivity of the analytical assay.

TABLE 4

| Budesonide Distribution in IPL Model and Recovery from Lungs | | | | | | | |
|---|---|---|---|---|---|---|---|
| BUD Distribution | Group-1 | Group-2 | Group-3 | Group-4 | Group-5 | Group-6 | Group-7 |
| Mass of Budesonide in Perfusate (in μg) | 11.2 | 8.3 | 6.4 | 10.7 | 3.9 | 7.4 | 5.2 |
| Mass of Budesonide Remaining in Lungs (in μg) | 3.3 | 4.3 | 3.7 | 12.8 | 0.6 | 2.1 | 12.9 |
| Total Budesonide Recovery Perfusate + Lung (in μg) | 14.5 | 12.6 | 10.1 | 23.5 | 4.5 | 9.5 | 18.1 |
| Theoretical Budesonide Nominal Dose (in μg) | 18.2 | 18.9 | 20.3 | 19.1 | 10.0 | 10.0 | 21.1 |
| Nominal Budesonide Dose Recovery (%) | 79.8 | 66.6 | 49.7 | 122.9 | 45.4 | 95.3 | 85.9 |
| Recovered Budesonide Ex-Lung (%) | 77.3 | 65.9 | 63.3 | 45.5 | 86.8 | 78.0 | 28.8 |

The measured budesonide concentrations were utilized to determine the time to maximum concentration (Tmax) and maximum concentration for each test formulation, and these parameters are reported in Table 5 below. Since the nominal dose for each of the Group-1, Group-2, Group-3, Group-4 and Group-7 formulations was twice the nominal dose of the Group-5 and Group-6 formulations, the reported Cmax was dose-normalized to provide a more accurate comparison between the seven test formulations. In addition, a single experimental run from the Group-1 and Group-4 pK data was removed for the purposes of the instant evaluation on the basis of unreliability, giving a different Cmax value for the two experimental groups as compared to the value reported above in Table 3. As can be seen, in the present analysis the Group-5 formulation had the largest Cmax, followed by the Group-2, Group-3 and Group-4 formulations. The Group-1, Group-6 and Group-7 formulations had comparable Cmax values ranging from about 40-58 ng/mL, and all three of these formulations had a delayed Tmax compared to the other four formulations. The range in Tmax values across all formulations was from 1.3 to 2.9 minutes.

TABLE 5

| Pharmacokinetic Analysis Revealing Tmax and Cmax of the Perfusate Analysis | | | |
|---|---|---|---|
| Formulation | Tmax (min) | Cmax (ng/ml) | Dose Normalized Cmax |
| Group-1 | 1.3 | 104.5 | 52.25 |
| Group-2 | 1.3 | 149.6 | 74.80 |
| Group-3 | 1.3 | 168.6 | 84.30 |
| Group-4 | 2.7 | 146.4 | 73.20 |
| Group-5 | 1.3 | 161.4 | — (161.40) |

TABLE 5-continued

| Pharmacokinetic Analysis Revealing Tmax and Cmax of the Perfusate Analysis | | | |
|---|---|---|---|
| Formulation | Tmax (min) | Cmax (ng/ml) | Dose Normalized Cmax |
| Group-6 | 2.7 | 58.2 | — (58.20) |
| Group-7 | 2.9 | 80.4 | 40.20 |

Figure 8:
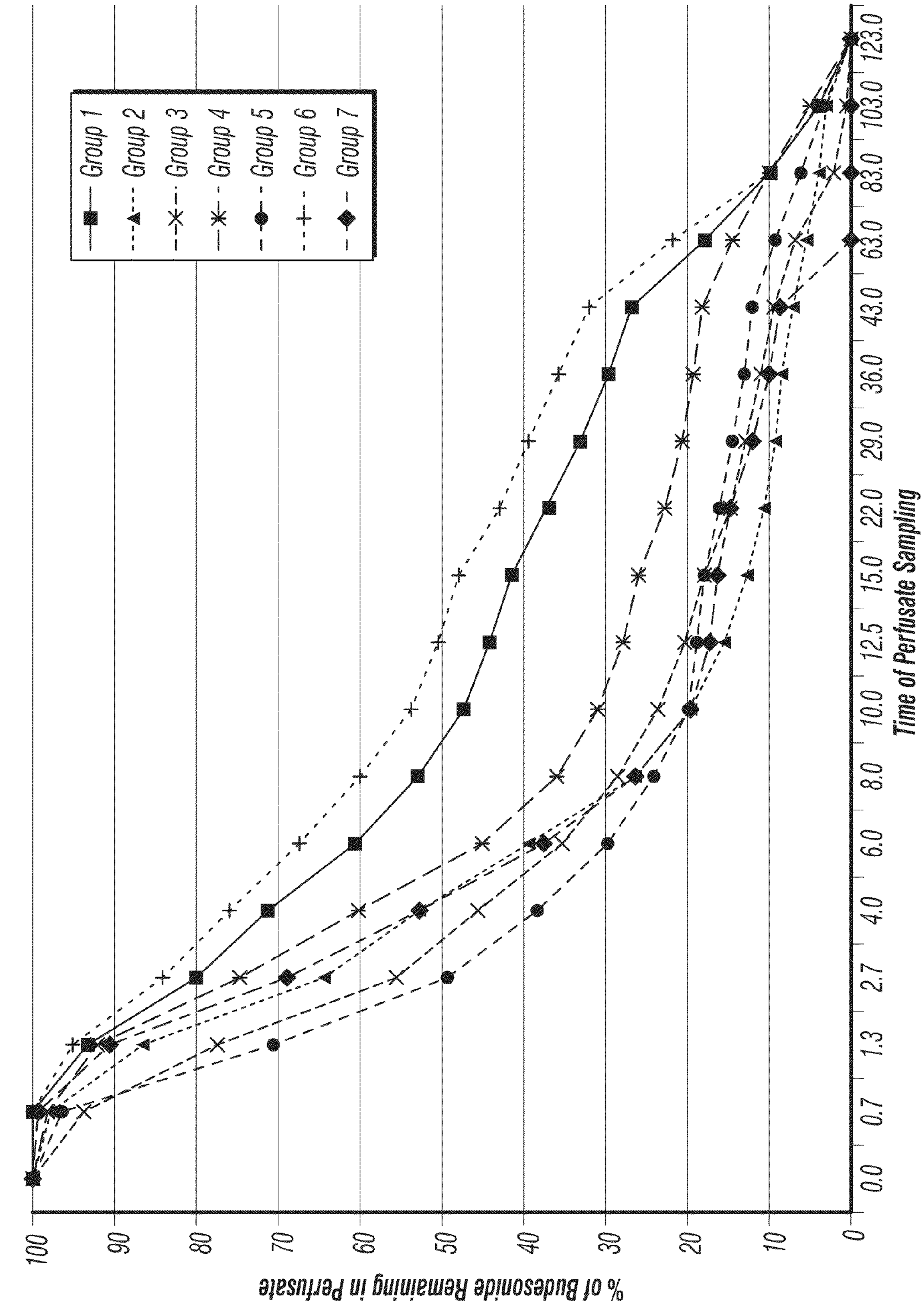
FIG. 8 depicts the concentration of budesonide in the perfusate for each of the seven budesonide test formulations evaluated as the percentage remaining over time as described in Example 6.

The concentration of budesonide in the perfusate was further evaluated as the percentage remaining over time for each of the test formulations, and the data are depicted in FIG. 8. For these data the total recovered budesonide was utilized as the initial concentration for each formulation. The amount of budesonide recovered at each time point was thus referenced to this initial concentration as a percentage. In this analysis, the Group-6 and Group-1 formulations had the slowest removal (rate) from the lung, and their clearance was similar. The removal and clearance of the remaining formulations had pretty significant overlap, with the Group-5 and Group-3 formulations being eliminated from the lung the quickest.

Figure 9:
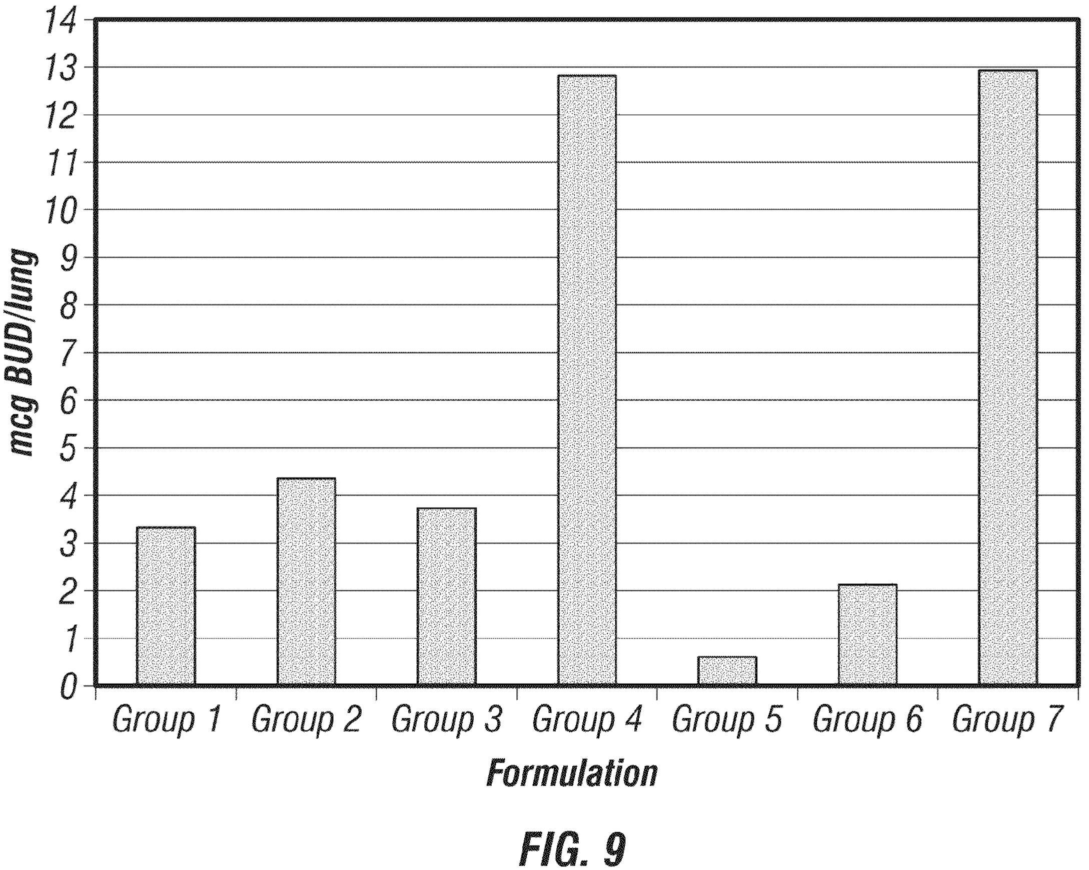
FIG. 9 depicts the average and standard error among tissue concentration of budesonide in the lungs for each of the seven test formulations at the completion of the lung perfusion study described in Example 6.

At the completion of the isolated perfused lung (IPL) study, the mass of budesonide (the average and standard error) among tissue in the lungs for each test formulation was measured, and these data are depicted in FIG. 9. The measured budesonide concentrations were variable among the formulations, but the data show increased lung retention of the Group-7 and Group-4 formulations (12.9 and 12.8 μg, respectively) as compared with the other test formulations (which ranged from 0.6 to 4.3 μg). The Group-5 formulation (the formulation with the smallest particle size) showed the lowest retention in the lung, followed by the Group-6 formulation. These data did not necessarily agree with the percentage remaining over time data (determined as a fraction of total measured budesonide in the perfusate, see FIG. 8) as determined above, suggesting that the removal rate kinetics for budesonide as determined strictly from such perfusate data does not appear to be an accurate predictor of total lung retention, at least in regard to the manner in which it was analyzed in this study.

CONCLUSIONS

Seven different budesonide particle suspension formulations were assessed for lung retention and the ability to cross the lung by perfusion in an isolated perfused lung system. LC-MS/MS was utilized to measure budesonide concentration in perfusates collected for up to approximately 103 minutes after administration of each test formulation. Budesonide remaining in the lung was also measured at the terminus of the procedure. The study and analysis showed that the various test formulations varied in both lung retention time and kinetics of removal into the perfusate. If particle size alone was responsible for overall lung retention, one would have expected that the Group-5 formulation with the smallest particle size (0.2-0.8 microns) would have the least lung retention, followed by the Group-1, Group-2, Group-4 and Group-7 formulations (particle sizes ranging from 1 to 5 microns), and finally that the Group-3 and Group-6 formulations (particle sizes ranging from 1 to 8 microns) would have the greatest lung retention. As expected, the Group-5 formulation did have the least amount of lung retention, however the Group-4 and Group-7 formulations (both containing the square bifrustum-shaped particles of the present invention) had the greatest lung retention despite having a relatively small particle size (2.5 microns), suggesting that the morphology (including reduced specific surface area (SSA)) of the square bifrustum particles provided for enhanced lung retention relative to similarly sized particle formulations (i.e., the Group-1 and Group-2 formulations), as well as relative to formulations with larger particle sizes (i.e., the Group-3 and Group-6 formulations). With regard to delivery kinetics, the Group-5 formulation had the highest overall (dose-normalized) Cmax value, a result that was supportive of the very low lung retention value seen for that formulation. However, the Group-2 (flake-shaped particles), Group-3 (spindle-shaped particles) and Group-4 (square bifrustum-shaped particles of the present invention) formulations all had dose-normalized Cmax values that were significantly higher than the Group-1 (micronized particles) and Group-6 (Pulmicort Respules, once-daily) formulations, while the Group-1 and Group-6 formulations appeared to have the slowest removal rate kinetics from the lung. Finally, the Group-6 (Pulmicort Respules, once-daily) and the Group-4 and Group-7 formulations (both containing the square bifrustum-shaped particles of the present invention) had the greatest Tmax values (ranging from 2.7 to 2.9 minutes) as compared with the other four experimental groups (1.3 minutes). Since all seven test formulations were substantially similar in all respects except for the budesonide particle morphology in the suspensions, these kinetic data are supportive of the theory that specific particle morphologies (e.g., particle size, SSA and aspect ratio) can affect drug delivery kinetics of budesonide across lung tissue.

While certain embodiments have been described herein, it will be understood by one skilled in the art that the compositions and methods of the present disclosure may be embodied in other specific forms without departing from the spirit thereof. The present embodiments are therefore to be considered in all respects as illustrative and not restrictive of the present disclosure. Rather, the scope and spirit of the present invention is embodied by the appended claims.

What is claimed is:

1. A method for forming a particulate budesonide composition, said method comprising:

(a) dissolving budesonide in a solvent comprising a mixture of water-miscible solvent and a partially water-miscible solvent to form a solution;

(b) combining the solution with an antisolvent containing a dispersion enhancer with agitation to produce particles of budesonide, wherein the particles of budesonide have a particle size distribution with mean diameter of from 1 to 10 microns, a specific surface area of from 1 to 3 $m^2/g$, and have a square bifrustum shape, with a mean largest dimension of less than 4 microns and a mean aspect ratio of less than 2.0.

2. The method of claim 1, wherein the particles have a mean diameter of from 1 to 3 microns.

3. The method of claim 1, wherein the particles have a specific surface area of from 2 to 3 $m^2/g$.

4. The method of claim 1, wherein the partially water-miscible solvent is selected from the group consisting of ethyl acetate, isopropyl acetate, diethyl ether, dichloromethane, methyl ethyl ketone, and methyl isobutyl ketone, or mixtures thereof.

5. The method of claim 4, wherein the partially water-miscible solvent is ethyl acetate.

6. The method of claim 1, wherein the water-miscible solvent is selected from the group consisting of acetone, acetonitrile, methanol, ethanol, isopropanol, dimethyl sulfoxide, or mixtures thereof.

7. The method of claim 6, wherein the water-miscible solvent is methanol.

8. The method of claim 1, wherein the water-miscible solvent comprises from 10 to 90% by volume of the solution.

9. The method of claim 8 wherein the water-miscible solvent is methanol and the partially-water miscible solvent is ethyl acetate.

10. The method of claim 9, wherein the solution comprises 50% by volume of methanol and 50% by volume of ethyl acetate.

11. The method of claim 1, wherein the antisolvent is water.

12. The method of claim 1 wherein the majority of the particles have a square bifrustum shape.

13. The method of claim 1, wherein the antisolvent contains 0.01 to 5 wt % of the dispersion enhancer.

14. The method of claim 13, wherein the dispersion enhancer is selected from the group consisting of polysorbate 20, polysorbate 40, polysorbate 60, polysorbate 80, polyethylene glycol, poloxamer, or mixtures thereof.

15. The method of claim 14, wherein the dispersion enhancer is polysorbate 80.

16. The method of claim 14, wherein the antisolvent contains about 0.05 w/v % polysorbate 80.

17. The method of claim 1, wherein agitation in step (b) is carried out under conditions of high shear or high pressure.

18. The method of claim 17, wherein agitation in step (b) is carried out using a rotor-stator or a high-pressure homogenizer apparatus.

19. The method of claim 1, wherein the antisolvent is at a temperature of from −10 to 50° C. when combined with the solution in step (b).

20. The method of claim 19, wherein the antisolvent is about 5° C. when combined with the solution in step (b).

21. The method of claim 1, wherein the antisolvent further contains one or more excipients selected from the group consisting of buffering agents, an isotonicity agent and an antioxidant.

22. The method of claim 1 further comprising one or more steps selected from the group consisting of sterile filtration of the solution and sterile filtration of the antisolvent.

23. Budesonide particles comprising:

crystalline particles of budesonide having a particle size distribution with mean diameter of 1 micron to 10 microns;

the particles further having a specific surface area of between 1 $m^2/g$ and 3 $m^2/g$; and the particles have a square bifrustum morphology with a mean largest dimension of less than 4 microns and a mean aspect ratio of less than 2.0.

24. The budesonide particles of claim 23, wherein the particles of budesonide have a mean diameter of 1 micron to 3 microns.

25. The budesonide particles of claim 23, wherein the square bifrustum-shaped particles have a specific surface area of between 2 $m^2/g$ and 3 $m^2/g$.

26. The budesonide particles of claim 23 wherein said particles exhibit an in-vitro dissolution rate of less than 90% of cumulative release after 1 minute when measured in a USP dissolution apparatus II, in 500 ml of simulated epithelial lung fluid at 37° C. and 75 rpm stirring rate, under sink conditions.

* * * * *

UNITED STATES PATENT AND TRADEMARK OFFICE

CERTIFICATE OF CORRECTION

PATENT NO. : 8,574,630 B2
APPLICATION NO. : 13/237792
DATED : November 5, 2013
INVENTOR(S) : Libo Wu et al.

It is certified that error appears in the above-identified patent and that said Letters Patent is hereby corrected as shown below:

On the Title page, in item (56), under "Other Publications", in column 2, line 2, delete "Wilkens," and insert -- Wilkins, --, therefor.

In the Drawings:

On sheet 3 of 11, line 1, delete "spaped" and insert -- shaped --, therefor.

On sheet 4 of 11, line 1, delete "spaped" and insert -- shaped --, therefor.

In the Specification:

In column 2, line 27, delete "Coorp.," and insert -- Corp., --, therefor.

In column 10, line 41, delete "antidoxidant" and insert -- antioxidant --, therefor.

In column 13, lines 42-43, delete "Medicnnsk" and insert -- Medicinsk --, therefor.

In column 13, line 55, delete "Coorp.," and insert -- Corp., --, therefor.

In column 18, line 33, delete "Budseonide" and insert -- Budesonide --, therefor.

In column 18, line 46, delete "Budseonide" and insert -- Budesonide --, therefor.

Signed and Sealed this
Twenty-fifth Day of February, 2014

Michelle K. Lee
*Deputy Director of the United States Patent and Trademark Office*